(12) United States Patent
Schwendeman et al.

(10) Patent No.: US 10,220,001 B2
(45) Date of Patent: Mar. 5, 2019

(54) ACTIVE SELF-HEALING BIOMATERIAL SYSTEM

(71) Applicant: The Regents of the University of Michigan, Ann Arbor, MI (US)

(72) Inventors: Steven P. Schwendeman, Superior Township, MI (US); Kashappa-Goud Desai, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/590,237

(22) Filed: Jan. 6, 2015

(65) Prior Publication Data
US 2015/0125531 A1 May 7, 2015

Related U.S. Application Data

(62) Division of application No. 13/512,913, filed as application No. PCT/US2011/021166 on Jan. 13, 2011.

(60) Provisional application No. 61/294,666, filed on Jan. 13, 2010.

(51) Int. Cl.
| | |
|---|---|
| *A61K 9/16* | (2006.01) |
| *A61K 38/38* | (2006.01) |
| *A61K 47/48* | (2006.01) |
| *A61K 38/09* | (2006.01) |
| *A61K 38/47* | (2006.01) |
| *A61K 39/08* | (2006.01) |

(52) U.S. Cl.
CPC .......... *A61K 9/1694* (2013.01); *A61K 9/1647* (2013.01); *A61K 38/09* (2013.01); *A61K 38/38* (2013.01); *A61K 38/385* (2013.01); *A61K 38/47* (2013.01); *A61K 39/08* (2013.01); *A61K 47/482* (2013.01); *A61K 47/48015* (2013.01); *A61K 47/48853* (2013.01); *A61K 47/48915* (2013.01)

(58) Field of Classification Search
None
See application file for complete search history.

(56) References Cited

U.S. PATENT DOCUMENTS

| | | | |
|---|---|---|---|
| 3,636,956 A * | 1/1972 | Schneider | ...... 606/224 |
| 5,389,376 A | 2/1995 | Duan et al. | |
| 5,656,298 A * | 8/1997 | Kitchell et al. | ...... 424/486 |
| 6,458,387 B1 | 10/2002 | Scott et al. | |
| 6,962,716 B1 | 11/2005 | King et al. | |
| 2002/0009493 A1 * | 1/2002 | Schwendeman et al. | ...... 424/486 |
| 2002/0045672 A1 | 4/2002 | Harris et al. | |
| 2008/0131478 A1 * | 6/2008 | Schwendeman et al. | ...... 424/424 |
| 2009/0274747 A1 | 11/2009 | Yasukochi et al. | |

FOREIGN PATENT DOCUMENTS

WO 01/28524 A1 4/2001

OTHER PUBLICATIONS

Sigma Aldrich, Albumin from Bovine Serum Product Information, 2000, p. 1-4.*
International Search Report and Written Opinion for PCT/US2011/021166, dated Oct. 24, 2011; ISA/KR.
Sigma Aldrich, Albumin from Bovine Serum Product Information, May 2, 2000.
Science Lab, Magnesium Carbonate MSDS, retrieved online on Jul. 30, 2014.
Daily Med, Vincristine Sulfate, http://dailymed.nim.nih.gov/dailymed/lookup.cfm?setid=49596de6-ab18-49d1-9e5b-30968fc21c36, retrieved online on Jul. 30, 2014.

* cited by examiner

*Primary Examiner* — Jennifer A Berrios
(74) *Attorney, Agent, or Firm* — Marshall, Gerstein & Borun LLP

(57) ABSTRACT

Methods and compositions are provided that load and encapsulate an agent, such as a protein, in a porous self-healing polymer. A delivery system includes a porous self-healing polymer, an ionic affinity trap within the pores of the self-healing polymer, and an agent associated with the ionic affinity trap. Methods of encapsulating an agent in a polymer include providing a porous self-healing polymer comprising an ionic affinity trap within the pores. The polymer is incubated with an agent having an affinity for the ionic affinity trap. At least a portion of the pores in the polymer are then healed. Active encapsulation of macromolecules at low concentrations may be achieved due to affinity of the agent for the ionic affinity trap within the pores.

13 Claims, 13 Drawing Sheets

A

B

A

B

ACTIVE SELF-HEALING BIOMATERIAL SYSTEM

CROSS-REFERENCE TO RELATED APPLICATIONS

Figure 1:
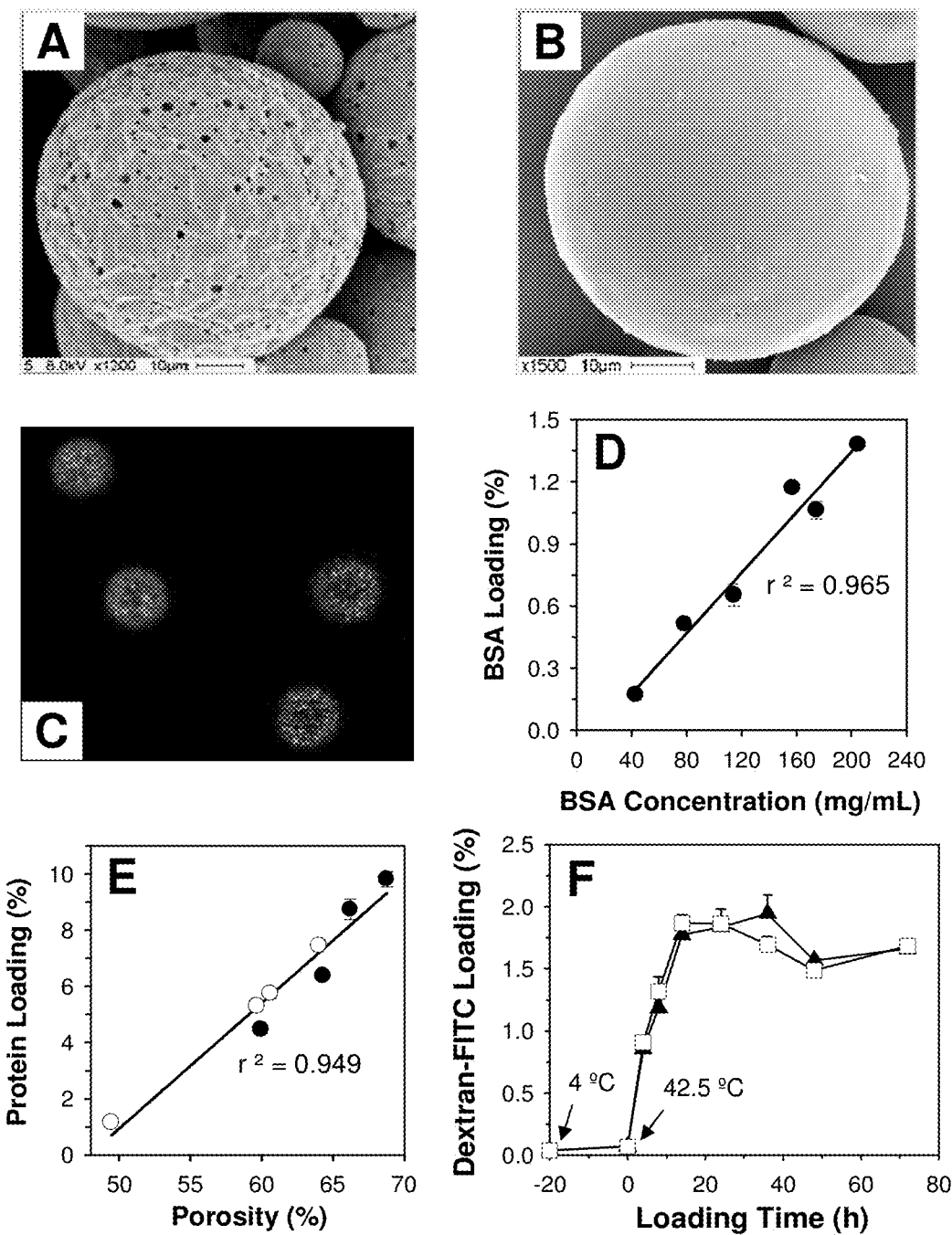

This application is a divisional of U.S. application Ser. No. 13/512,913 filed May 31, 2012, which is a 371 U.S. National Stage of International Application No. PCT/US2011/021166, filed Jan. 13, 2011, and claims the benefit of United States Provisional Application No. 61/294,666, filed on Jan. 13, 2010, the disclosures of which are herein incorporated by reference in their entirety.

GOVERNMENT RIGHTS

This invention was made with U.S. government support under grant number R21 EB008873 awarded by the National Institutes of Health. The U.S. government has certain rights in the invention.

FIELD

The present technology relates to a delivery system with high encapsulation efficiency for an agent such as a biomolecule.

INTRODUCTION

Injectable biodegradable polymeric particles, such as microspheres, provide a means to deliver and control the release of molecules such as drugs, proteins, peptides, and vaccine antigens. Once injected, the biodegradable polymeric particles can release the molecule over the course of hours, days, or even weeks to months, providing a distinct advantage over daily injections in terms of patient acceptability and compliance. For example, controlled release of a protein antigen can reduce the number of doses in an immunization schedule and can optimize the desired immune response via selective targeting of antigen to antigen presenting cells. Several biodegradable polymers have been explored for the microencapsulation and delivery of macromolecules. Copolymers of lactic acid and glycolic acid (PLGA) are one type of biodegradable polymer used in pharmaceutical products or medical devices including several approved by the U.S. Food and Drug Administration. For example, PLGAs are used in commercially available controlled-release peptide delivery systems, including the Lupron Depot™ (leuprolide acetate), Sandostatin LAR™ (octreotide acetate), and Zoladex™ implant (goserelin acetate).

Unfortunately, successful controlled release of macromolecules such as proteins can be difficult. Stability of the protein during encapsulation and stability during release in vivo are two concerns. And slowly and completely releasing therapeutic proteins in their native state from biodegradable polymeric particles can pose a significant obstacle in the development of controlled-release injectable depots. Methods for encapsulating macromolecules in biodegradable polymers can involve harsh processing conditions, including exposure to organic solvents, excess heat, homogenization including mixing, sonication, and high-speed agitation, and so forth, which alone or in combination can denature and/or destabilize proteins and other macromolecules. Additionally, drying and micronization of the macromolecule prior to encapsulation may further destabilize the macromolecule.

What is more, hydrophilic macromolecules, including many proteins, cannot readily diffuse through a hydrophobic polymer phase, such as PLGA. The release of encapsulated protein drugs from PLGA requires at some point the diffusion of the macromolecules through water-filled pores and channels. For example, protein release from PLGA microspheres can exhibit tri-phasic behavior. First, protein on the surface or having access to the surface of microspheres (i.e., in open pores) is released rapidly, providing an initial burst release. Second, a time lag commonly exists as the protein cannot diffuse through the polymer phase. Third, a continuous release of protein occurs following polymer erosion so that more pores and channels are formed allowing protein in previously isolated pores to be released. There are few exceptions to the low permeability rule (i.e., peptides and proteins cannot diffuse through PLGA) not commonly known, which occur for example, when lower MW PLGAs with acid end groups take up water. In this case, the polymer may also sorb peptides of moderate MW deep into the polymer phase itself.

Encapsulation methods employing self-healing polymers have been developed to form biodegradable polymeric particles loaded with various macromolecules; e.g., peptides, proteins, DNA, siRNA, etc. U.S. Pat. Appl. Pub. 2008/0131478 to Schwendeman et al. describes methods that obviate damaging stresses during microencapsulation, which include forming a porous polymer, ideally with a percolating pore network, incubating an aqueous solution of the macromolecules below the glass transition temperature ($T_g$) of the polymer so that the macromolecule is taken up into the pores of the polymer, and raising the temperature above the $T_g$ so that the polymer pores close irreversibly encapsulating the macromolecule. Other methods can be used to close the pores besides temperature change. For example, exposure to solvent, such as alcohol vapor, can be used to facilitate self-healing of the polymer. Using this methodology, loadings of about 10% w/w or more can be achieved.

Passive encapsulation methods rely on equilibration of the protein between the solution outside the polymer and the aqueous pores inside the polymer. Such methods may not provide high encapsulation efficiency; i.e., mass macromolecule encapsulated/mass of macromolecule charged to the system. As a result, a significant proportion of the macromolecule to be loaded remains in solution outside the polymer as the polymer pores close. The macromolecule solution may have to be reused multiple times in this case to avoid wasting the macromolecule. Furthermore, passive encapsulation typically requires very high concentrations of the macromolecule (e.g., >100 mg/mL) in order to achieve elevated loading. Some macromolecules may have limited solubility, prohibiting this method altogether.

Accordingly, a need exists for new methods of encapsulating macromolecules in pore-containing polymers, such as PLGA, that can increase the loading and encapsulation efficiency. It is desirable that the method could operated without the need for organic solvent or other harsh processing conditions during encapsulation, which can denature proteins, for example, and destabilize macromolecules. It is also desirable that there would be no need for micronization of the macromolecule, such as protein or nucleic acid, before encapsulation and is desirable that there would be no need for drying, each of which can destabilize macromolecules. The encapsulation method should be less expensive to carry out than conventional methods, where cost may be a principal factor in the slow development of controlled release injectable depots. For example, passive loading of polymer particles may waste a considerable amount of macromolecule, leaving a majority of the macromolecule in the solution following pore closure.

SUMMARY

The present technology includes systems, methods, articles, and compositions that relate to sorbing and/or encapsulating an agent, such as a biomolecule, with a solid polymer, such as a porous self-healing polymer, where the polymer may be in the form of particles or microspheres. The delivery system may also take on various forms, may be a portion of other forms, or may be coated onto other forms, including various shapes or devices such as drug eluting stents, sutures, screws, tissue engineering scaffolds, and blood circulating nanoparticles, among others.

In some embodiments, a delivery system comprises a solid polymer matrix comprising an ionic affinity trap, the ionic affinity trap is operable to sorb an agent from an aqueous solution. An agent can be sorbed to the ionic affinity trap. The solid polymer matrix can be a self-healing polymer. The self-healing polymer can comprise one or more pores that comprise the ionic affinity trap, where at least a portion of the pores can be interconnected. The delivery system can further include an agent sorbed to the ionic affinity trap and wherein the pore partially or fully encapsulates the agent and prevents the agent from exiting the pore. The solid polymer matrix can comprises a biodegradable polymer and can comprise a copolymer of lactic acid and glycolic acid. The solid polymer matrix can take the form of a microparticle or microsphere. The ionic affinity trap can comprise a metal salt, such as aluminum hydroxide, aluminum phosphate, potassium phosphate, magnesium carbonate, calcium phosphate, or combinations thereof, and can comprise an ionomer gel. The ionic affinity trap can comprise ionized end groups of the polymer, where the ionized end groups can comprise carboxylate groups. The agent can comprise a biomolecule, drug, or antigen, where the biomolecule can comprise a protein, peptide, proteoglycan, lipoprotein, or nucleic acid. The agent can also comprise an immunocontraceptive. The solid polymer matrix can further comprise a plasticizer.

In some embodiments, a method of making a delivery system comprises sorbing an agent to an ionic affinity trap, wherein a solid polymer matrix comprises the ionic affinity trap and an aqueous solution comprises the agent. The method can further comprise partially or fully encapsulating an agent in a pore by increasing the temperature of the self-healing polymer to about its $T_g$ or above, where the solid polymer matrix includes a self-healing polymer comprising the pore. The aqueous solution in the sorbing step can comprise less than about 1 mg/mL of the agent. At least 90% of the agent in the sorbing step can be sorbed to the ionic affinity trap.

In some embodiments, a delivery system can include a self-healing polymer comprising one or more pores, where the pore or pores include an ionic affinity trap and an agent, such as a biomolecule, associated with the ionic affinity trap. The delivery system can be made by providing the self-healing polymer having one or more pores, where the pore(s) includes an ionic affinity trap. The self-healing polymer is contacted with an agent having affinity for the ionic affinity trap so that the agent associates with the ionic affinity trap. The self-healing polymer can then partially or fully encapsulate the agent, preventing the agent from exiting the pore(s). The delivery system can also include a self-healing polymer where a portion of the self-healing polymer comprises ionized end groups and an agent sorbed to the ionized end groups. Such a delivery system can be made by contacting the self-healing polymer with an agent having affinity for the ionized end groups and optionally Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1. Self-healing microencapsulation of large molecules in PLGA micro sphere injectable controlled-release depots. Scanning electron micrographs of self-microencapsulating microspheres (SM-1, Tables 1 and 2) before (A) and after (B) healing of polymer pores in the presence of 230 mg/mL lysozyme at 42.5° C. Laser confocal fluorescent micrographs (C) of the cross-sectional distribution of BSA-Coumarin (in white domains) after self-healing encapsulation of the protein in microspheres (20-63 μm in diameter) (SM-2, Tables 1 and 2). Increasing protein loading by increasing protein concentration exposed to SM-micro spheres (D) (SM-2, Tables 1 and 2) or SM-micro sphere porosity (E) with an increasing volume (25, 100, 200, and 350 μL, open circles) of inner water phase in the double emulsion or amount (0, 1.5, 4.3, and 11% w/w $MgCO_3$, closed circles) of porosigen (SM-3, Tables 1 and 2). Kinetics of self-encapsulation of large molecule in PLGA microspheres (SM-3, Tables 1 and 2) after initiating self-healing with increase of $T>T_g$ (F). SM microspheres were first incubated at 4° C. for 20 h and then at 42.5° C. (time=0 h) with 65 mg/mL dextran-FITC. Values represent mean±SEM, n=3 (F) or 5 (D and E) measurements.

Figure 2:
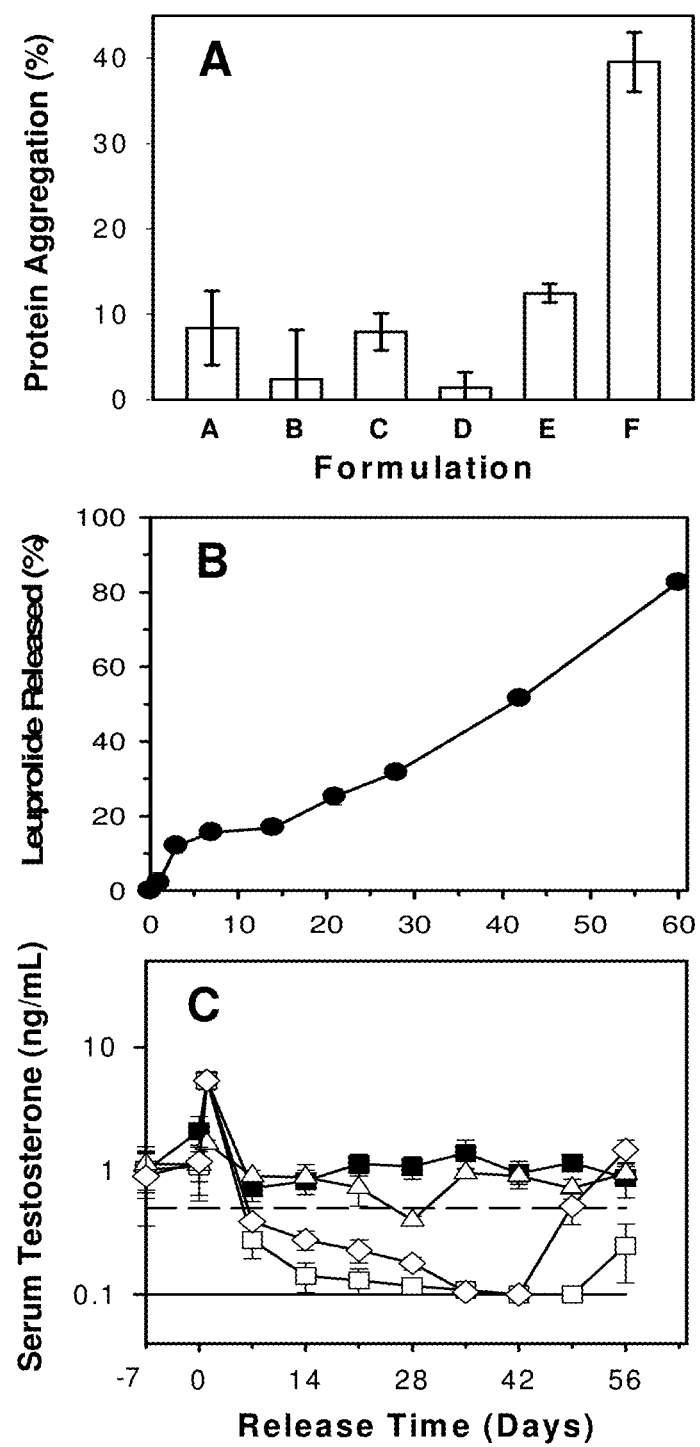

FIG. 2. Assessment of lysozyme aggregation and leuprolide controlled release after self-healing microencapsulation (SM) without organic solvent. Insoluble aggregation recorded after microencapsulation of encapsulation-labile lysozyme (A) according to self-healing (Formulations A-D without organic solvent) and standard solvent-evaporation (Formulations E and F with organic solvent) processes. SM microspheres were prepared from 11 (Formulations A, and B) and 51 (Formulations C-F) kDa $M_w$ PLGA 50/50, and in the presence (B, D, F) and absence (A, C, E) of 0.45 M sucrose in the aqueous lysozyme solution. A: Formulations A and B, C and D, and E and F, respectively, correspond to SM-4, SM-3, and TM-1 in Tables 1 and 2. In vitro and in vivo evaluation of controlled-release leuprolide from SM-microspheres (SM-5, Tables 1 and 2). Slow release of leuprolide was observed in a physiological buffer in vitro (B) and as indicated by serum testosterone suppression in rats (C). Animals were injected subcutaneously once with 1-month dose of soluble leuprolide (filled squares), once with 2-month dose of leuprolide acetate in SM-microspheres (open diamonds), twice (day 0 and day 28) with commercial 1-month Lupron Depot™ (open squares) or once with blank SM-microspheres containing no drug (open triangles). Dose was based on 100 μg/kg/day. Solid and dashed line respectively represents lower testosterone detection limit (0.1 ng/mL) and castration level (0.5 ng/mL), respectively. Values represent mean±SEM, n=5 measurements (A and B) or 6 animals (C).

Figure 3:
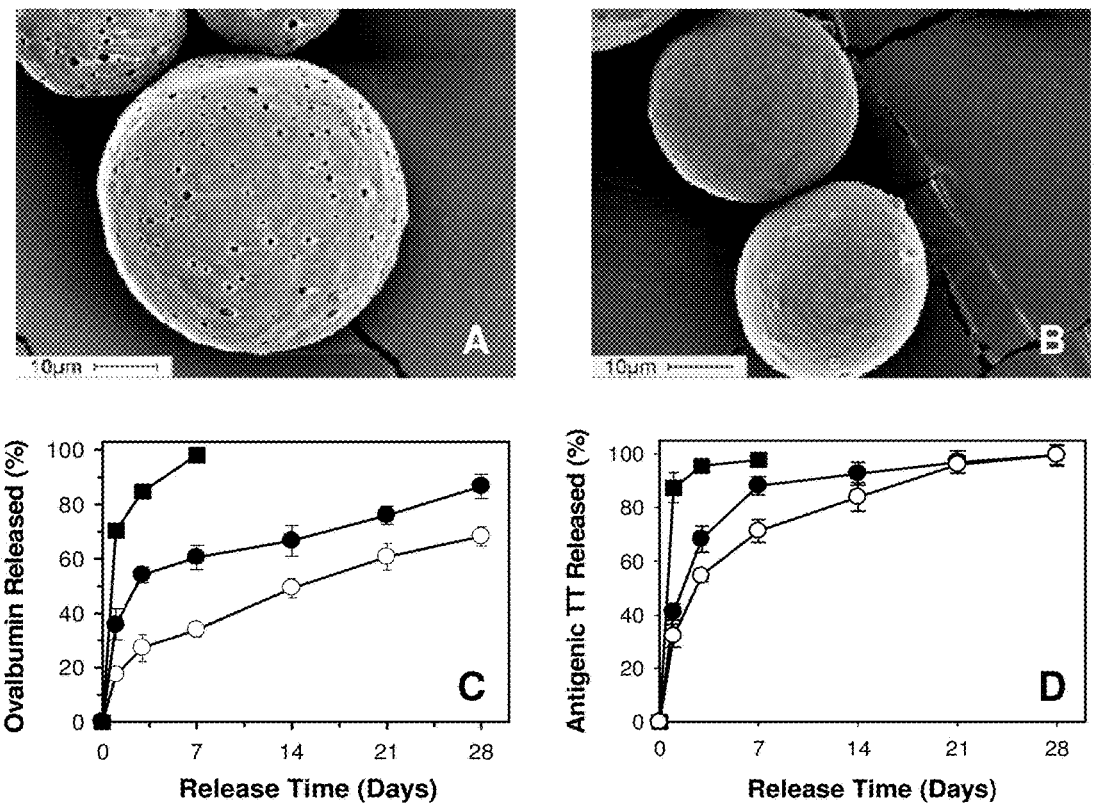

FIG. 3. Active self-microencapsulation of ovalbumin (OVA) and tetanus toxoid (TT) in Al(OH)$_3$ adjuvant-containing SM-microspheres (ASM, Tables 1 and 2). Scanning electron micrographs (A, B) depict the SM-microsphere morphology after loading entire OVA mass from 0.5 mg/mL OVA solution and self-healing at 37° C. PLGA plasticized with 0% (A) and 5% (B) diethyl phthalate (DEP). A and B formulations respectively correspond to ASM-1 and ASM-3 in Tables 1-4. Controlled release of OVA monomer (C) or antigenic TT (D) from active self-microencapsulating microspheres relative to OVA or TT-loaded aluminum adjuvant without polymer (closed squares, Al(OH)$_3$ no PLGA; closed circles, 3.2% Al(OH)$_3$/3.5% trehalose/PLGA no plasticizer (ASM-1, tables S1-S5); open circles, 3.2% Al(OH)$_3$/3.5% trehalose/PLGA/5% DEP). Closed and open circles respectively represent formulation ASM-1 and ASM-3 in Tables 1-5. Values represent mean±SEM, n=3 measurements.

Figure 4:
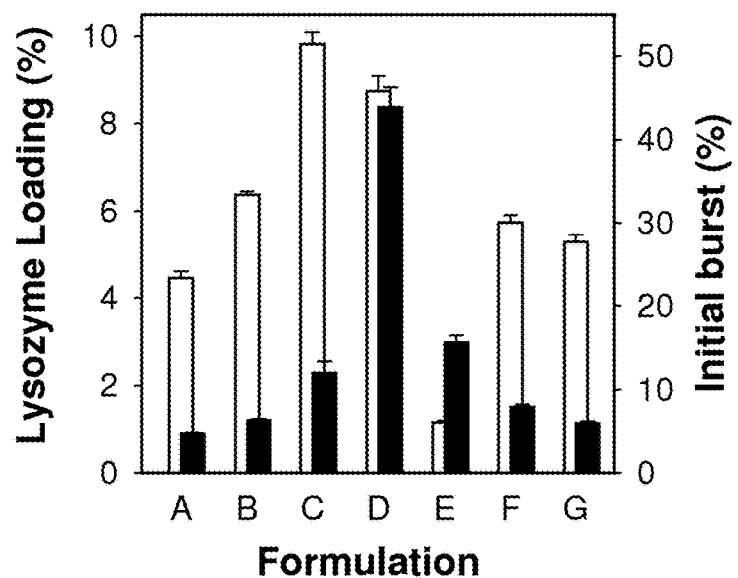

FIG. 4. Goodness of self-encapsulation in PLGA microspheres as indicated by elevated lysozyme loading (open bar chart) and minimal initial burst (closed bar chart) of enzyme employing diversity of pore-forming excipients/initial water phase volume to create the PLGA 50/50 pore network. Formulations A, B, C, and D were respectively prepared with 0, 1.5, 4.3, and 11% w/w MgCO$_3$ and E, F, and G were respectively prepared with 25, 100, and 350 µL initial water phase (SM-3, Tables 1 and 2). Values represent mean±SEM, n=3 measurements.

Figure 5:
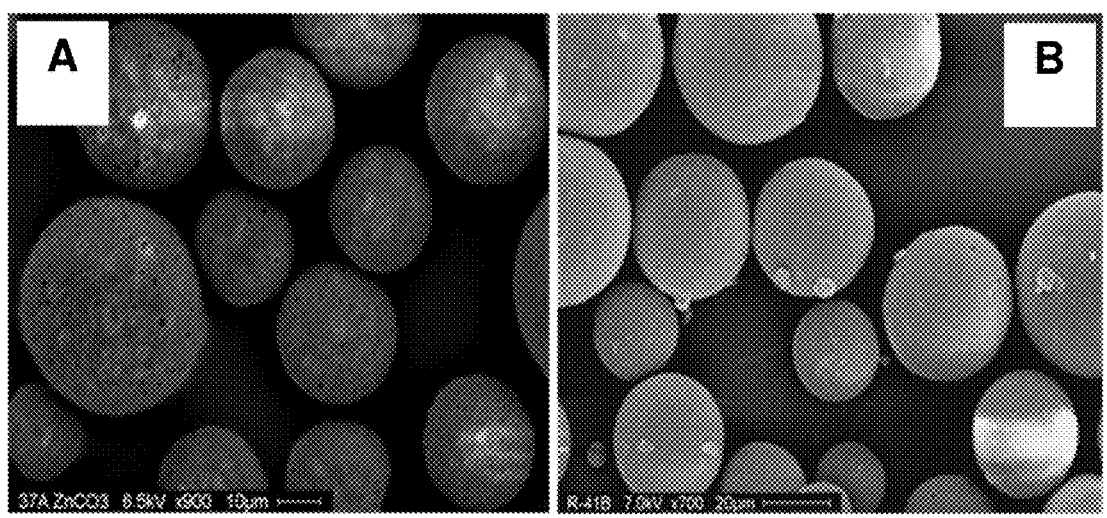

FIG. 5. Self-healing microencapsulation of leuprolide acetate in PLGA 50:50 ($M_w$=51 kDa) microspheres (SM-5, Tables 1 and 2). Scanning electron microscopy image of SM PLGA microspheres before (A) and after (B) self-healing microencapsulation of leuprolide acetate. Actual amount of leuprolide acetate self-encapsulated by this formulation was 3.0±0.2% (w/w peptide/polymer matrix) (5 measurements).

Figure 6:
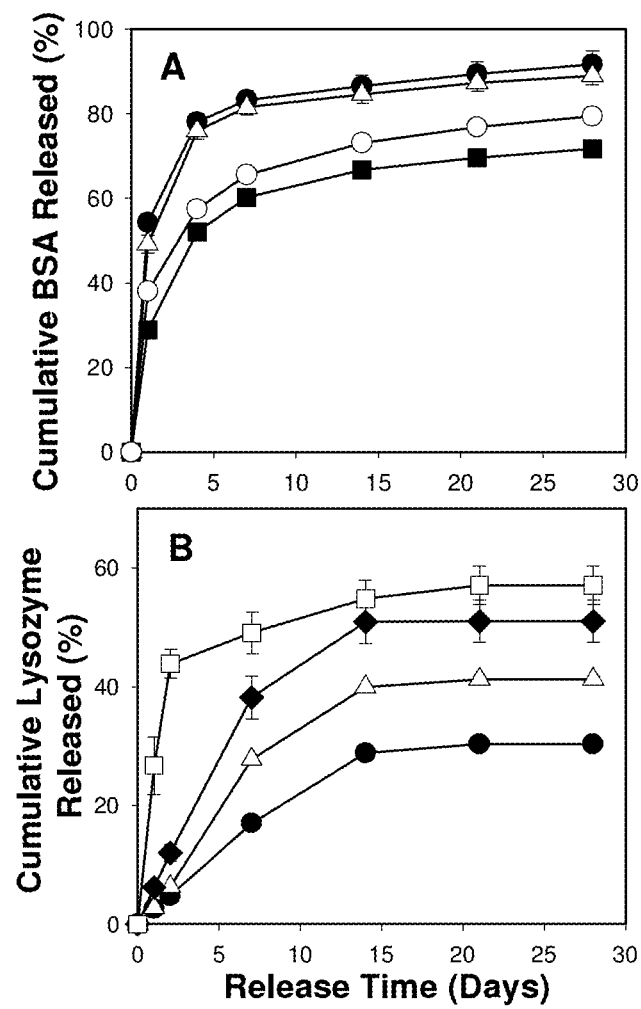

FIG. 6. Protection of protein (BSA and lysozyme) against acid-induced instability during release from self-microencapsulated PLGA 50:50 ($M_w$=51 kDa) microspheres (SM-3, Tables 1 and 2). (A) Effect of MgCO$_3$ (porosigen/stabilizer) loading (3 (●) and 4.5 (Δ) % w/w) and addition of sucrose (0 (■) and 0.45 (○) M) in protein loading solution on cumulative release of BSA from self-microencapsulated microspheres. Actual BSA loading in ●, Δ, ■, and ○ SM formulations was 4.25±0.05, 5.65±0.06, 7.26±0.09, and 5.54±0.04%, respectively. Initial water phase (200 µL) was PBS (pH 7.4) with (■ and ○) or without trehalose (500 mg in 1 g PBS). (B) Effect of MgCO$_3$ (porosigen/stabilizer) loading (0 (●), 1.5 (Δ), 4.5 (♦), and 11 (□) % w/w) on cumulative release of lysozyme from self-microencapsulated microspheres. Actual lysozyme loading in ●, Δ, ♦, and □ SM formulations was 4.2±0.2, 6.4±0.1, 9.8±0.3, and 8.7±0.4%, respectively. In vitro release studies were conducted in PBST at 37° C. and symbols represent mean±SEM (three measurements).

Figure 7:
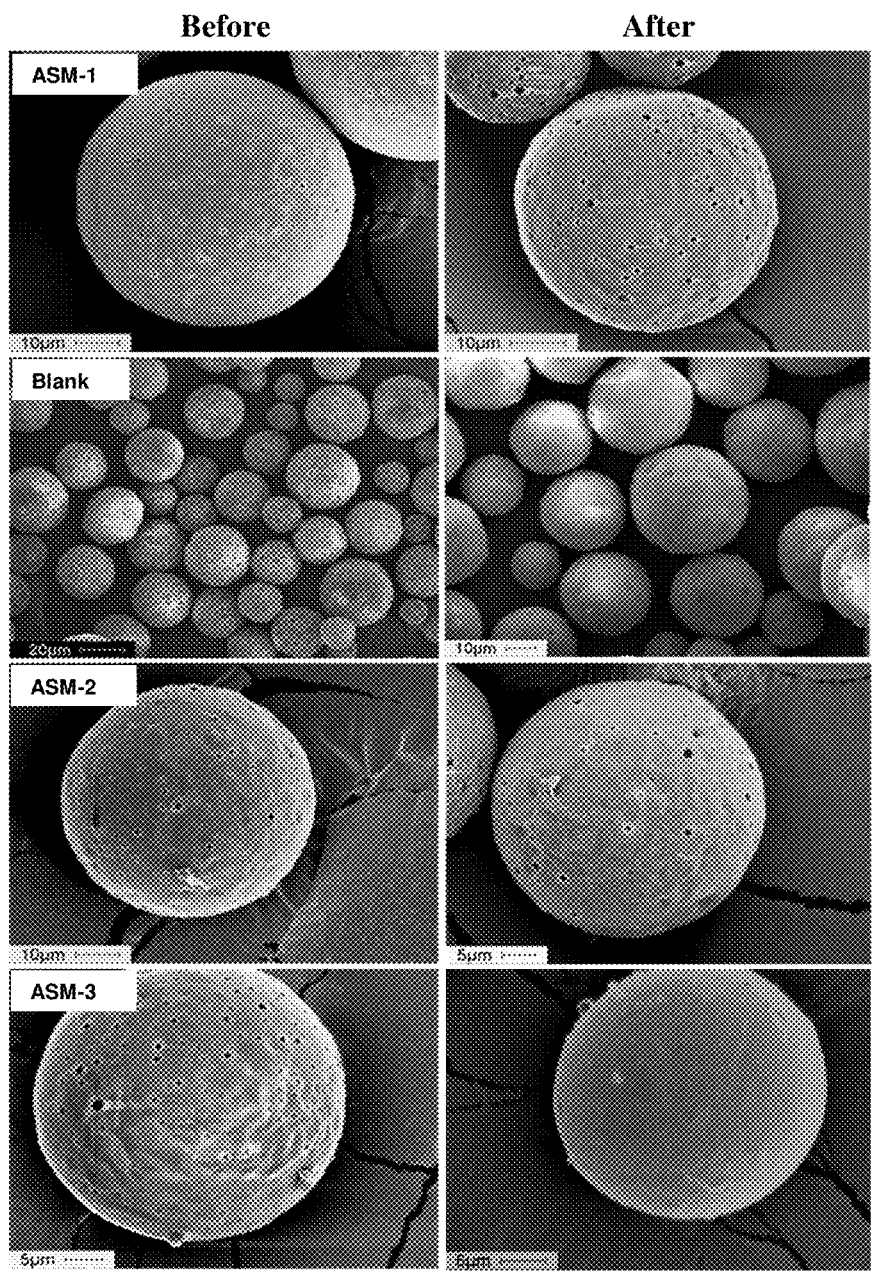

FIG. 7. Effect of encapsulation of Al(OH)$_3$ and blending of hydrophobic plasticizer (diethyl phthalate (DEP)) on the self-healing phenomenon of PLGA 50:50 ($M_w$=51 kDa) microspheres. Surface morphology of blank (3.5% w/w trehalose loaded), ASM-1, ASM-2, and ASM-3 PLGA microspheres before and after self-healing microencapsulation process. ASM-1, ASM-2, and ASM-3 PLGA microsphere formulations consists of 3.2% w/w Al(OH)$_3$ and 3.5% w/w trehalose as porosigen and Al(OH)$_3$ lyophilization stabilizer. ASM-2 and ASM-3 contain 2.5 and 5% w/w DEP, respectively. Blank and ASM-1 PLGA microspheres were incubated at 25 and 43° C. for 48 h. ASM-2 and ASM-3 PLGA microspheres were incubated for 48, 24, and 30 h at 10, 25, and 37° C., respectively. Preparation process of blank ASM PLGA microspheres is given in Table 1.

Figure 8:
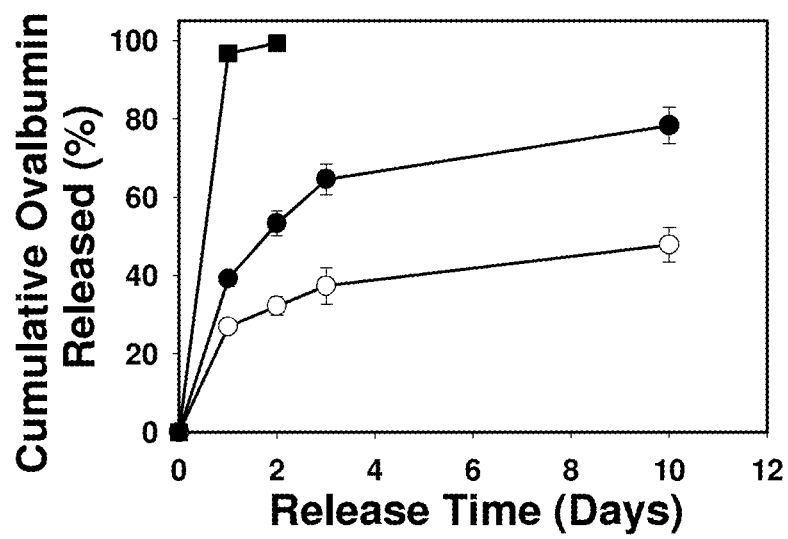

FIG. 8. Evaluation of quality of active protein self-microencapsulation in Al(OH)$_3$-PLGA 50:50 ($M_w$=51 kDa) (ASM PLGA) microspheres in 190 mM sodium citrate solution. Cumulative ovalbumin released as a function of time from unencapsulated Al(OH)$_3$ gel (control) (■) and with (○) (ASM-3, Tables 3 and 4) and without (●) (ASM-1, Tables 3 and 4) 5% w/w DEP in Al(OH)$_3$-PLGA microsphere formulations. In vitro release studies were conducted at 37° C. and symbols represent mean±SEM (three measurements).

Figure 9:
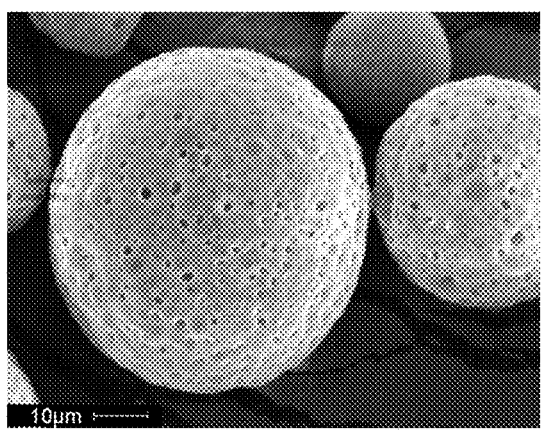
Figure 9:
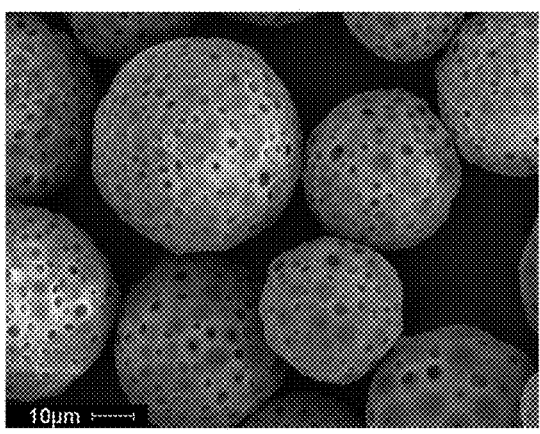

FIG. 9. Photomicrographs of 3.2 wt % alhydrogel/3.8 wt % trehalose/PLGA microparticles before (A) and after (B) self-healing at 25° C. for 24 h and 43° C. for 48 h.

Figure 10:
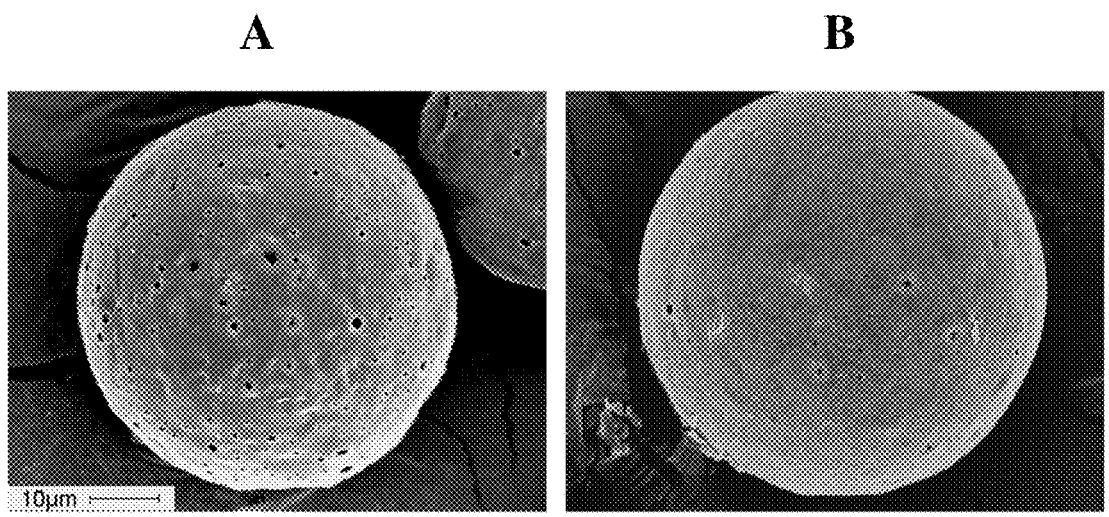

FIG. 10. Photomicrographs of 3.2 wt % alhydrogel/3.8 wt % trehalose/2.5 wt % DEP/PLGA microparticles before (A) and after (B) self-healing at 10° C. for 48 h, 25° C. for 24 h, and 37° C. for 30 h.

Figure 11:
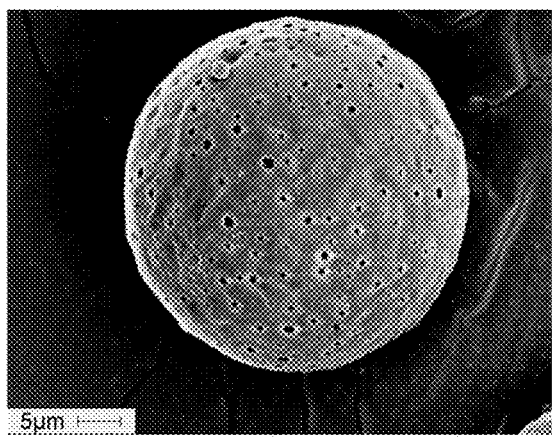
Figure 11:
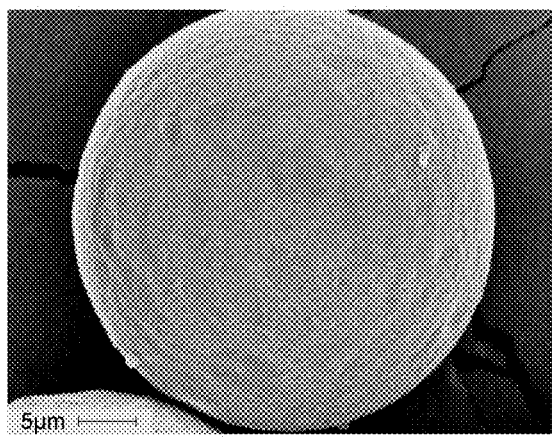

FIG. 11. Photomicrographs of 3.2 wt % Alhydrogel/3.8 wt % Trehalose/5 wt % DEP/PLGA microparticles before (A) and after (B) self-healing.

Figure 12:
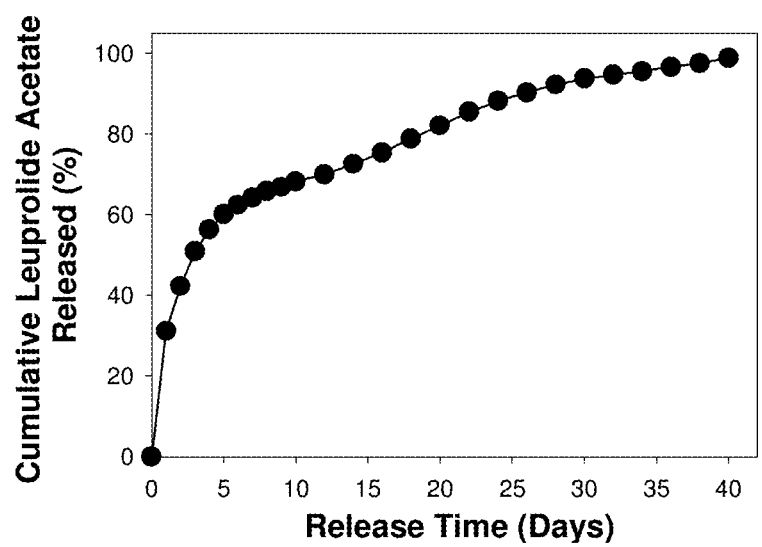

FIG. 12. Evaluation of in vitro release of leuprolide acetate (LA) from LA-PLGA particles. Cumulative amount of LA released as a function of incubation time in PBST at 37° C. The actual loading of LA in LA-PLGA particles was about 17 wt %. Symbols represent mean±SE, n=3.

Figure 13:
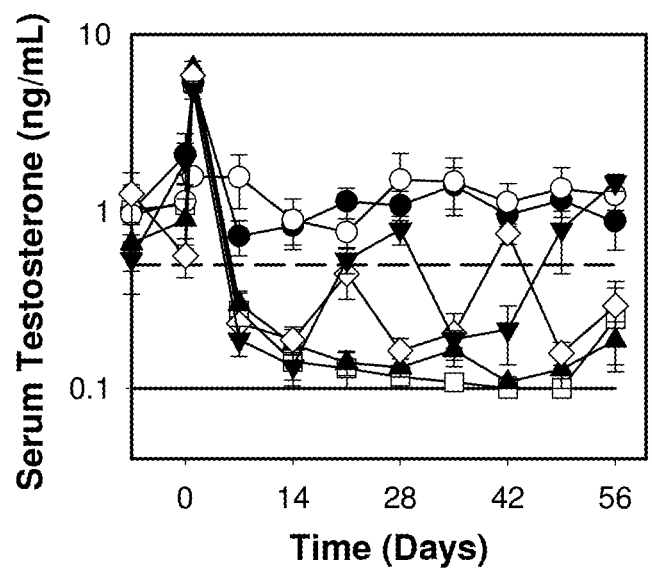

FIG. 13. Prolonged serum testosterone suppression by leuprolide acetate (LA)-PLGA particles in male Sprague-Dawley rats. Effect of dosing interval (2×, 3×, and 4×) of LA-PLGA particles on serum testosterone suppression. Animals were injected subcutaneously with 1× (day 0) soluble leuprolide (●), LA-PLGA particles with different dosing interval (2×: day 0, 14, 28, and 42 (▲), 3×: day 21 and 42 (◇), and 4×: day 0 and 28 (▼)), and blank PLGA particles (○) in a liquid vehicle (1% w/v carboxymethylcellulose and 2% w/v mannitol) along with 2× (day 0 and 28) commercial 1-month Lupron Depot (□). The dose of leuprolide acetate was 100 µg/kg/day. Solid and dashed line respectively represents lower testosterone detection limit and castration level. Symbols represent mean±SEM, n=6. Lowest detection limit of testosterone was 0.1 ng/mL.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

Preparation of controlled-release polymeric biomaterials generally requires an organic solvent during drug microencapsulation, limiting both biomaterial design and applications for large molecular drugs. The present technology provides a new microencapsulation paradigm based on spontaneous self-healing of polymers. For example, biomolecules such as peptides, proteins, or polysaccharides dissolved in aqueous solution can be self-microencapsulated in poly(lactic-co-glycolic acid) (PLGA) by placing the biomacromolecule solution in contact with solid PLGA, preformed with an interconnected pore-network, at below the polymer glass transition temperature ($T_g$), and then healing the pores at a temperature at or above the $T_g$. Healed polymers can then slowly release the biomacromolecules under physiological conditions for over 1 month. Benefits of the present approach include improved compatibility with biotechnology-derived drugs, reduced manufacturing cost and residual organic solvent, the ability to create new biomaterial architectures, and facile use among non-formulation scientists and clinicians.

Modern synthetic polymeric biomaterials are widely used to slowly release medicines over days to years after administration to the body. These polymers are configured in numerous biomedical and pharmaceutical three-dimensional forms (e.g., spheres, rods, coatings, porous matrices) including micro- to millimeter scale injectable depots, drug-eluting stents, scaffolds for engineering tissues, and blood-circulating nanometer scale particles and can be made biodegradable or nondegradable. Until now, drugs, particularly peptides and proteins, are most commonly microencapsulated by first combining drug with a polymer dissolved in organic solvent. Before or after this combination the drug is either micronized (e.g., by homogenization, sonication, or grinding) or molecularly dissolved in the solvent, to yield drug domains, which later become dispersed in the final polymer matrix. Both steps can compromise stability of encapsulated proteins and other biomolecules. The organic solvent is removed to clinically acceptable levels and the polymer is dried before use. Described here is a new self-microencapsulation paradigm based on the polymer's own spontaneous "self-healing" capacity in aqueous media. Features of this new approach include a simple mixing process (e.g., as mixing naked DNA to lipofectin gene delivery vector), the absence of exposure of drug to organic solvent during encapsulation (e.g., as supercritical fluid polymer processing), and mild processing conditions (e.g., as spray-congealing for commercial manufacture of PLGA-encapsulated growth hormone).

To illustrate this new paradigm, injectable self-microencapsulating (SM) microsphere (SM-1, Table 1) depots of biocompatible copolymers of lactic and glycolic acids (PLGA) were prepared by a standard emulsion-based method with leachable trehalose to create interconnected porous network in the polymer, but without including an agent such as a biomolecule or drug. After leaching the sugar, pores on the scale of 250 to 2500 nm were easily viewed by electron microscopy (FIG. 1A). The dry microspheres were incubated at 4° C. (<<hydrated $T_g$~30° C.) in concentrated aqueous lysozyme solution at 230 mg/mL for 48 h to allow the protein to enter the open polymer pores. Self-healing of the pores was initiated without organic solvent by raising the temperature to about or greater than the $T_g$ to 42.5° C. for 44 h (SM-1, Table 2), resulting in lysozyme-encapsulated microspheres with 3.8±0.1% protein loading (w/w protein/polymer matrix, 5 measurements) and a nonporous polymer surface (FIG. 1B).

Large molecules penetrate deep within the polymer matrix prepared by this method, as viewed by laser scanning confocal micrographs of healed SM microspheres prepared with fluorescent coumarin-labelled BSA (FIG. 1C). Moreover, molecules as large as 2 million Da were found to enter the polymer pore network and become self-encapsulated, as indicated by the similar loading in the polymer of 2 MDa and 4 kDa fluorescent-labeled dextrans. Protein loading determined after extensive washing of SM microspheres was found easily adjustable, for example, as seen by the sensitivity of BSA (FIG. 1D) and lysozyme (FIG. 1E) loading, respectively, to initial protein loading solution concentration (SM-2, Tables 1 and 2) and dry SM polymer porosity (SM-3, Tables 1 and 2). To test the goodness of encapsulation, SM microspheres prepared by several different conditions were loaded with protein and incubated under physiological conditions (in PBS+0.02% Tween 80, pH 7.4 at 37° C.) for 48 h to observe the "initial burst release" of protein (FIG. 4), which is often too high with poorly encapsulated material. SM microspheres with elevated protein loading of 1.2±0.1 to 9.8±0.3% (5 measurements) and optimal porosigen loading (e.g., 1.5-4.5% (w/w magnesium carbonate/polymer matrix), 5 measurements) typically exhibited an optimal initial burst release of protein (<20% release). Importantly, the measured loading and initial burst values were within the desirable range as established by clinically used PLGA depots and required loading times were on the order of 12 hours (FIG. 1F).

As expected by the mild encapsulation conditions (37-43° C. temperature exposure) by the new approach—no harsh mixing or organic solvent exposure—protein stability was also improved with SM microspheres relative to microspheres prepared by traditional emulsion-based microencapsulation techniques (e.g., water-in-oil-in-water—solvent evaporation, w/o/w, as used for the Lupron Depot). For example, using the model enzyme, lysozyme, well-established to undergo aggregation during solvent evaporation, the potential stability improvement of the enzyme in SM microspheres was evaluated relative to solvent evaporation control groups. In formulations with two different MW polymers with and without addition of protein-stabilizing sucrose, the stability of lysozyme was improved with SM microspheres in each case (FIG. 2A), and when loading by self-healing in the presence of sucrose, negligible aggregation or activity losses of the enzyme were detected.

Desirable polypeptides were also successfully self-microencapsulated by PLGAs and released slowly and continuously over a period of >1 month. For example, the most commonly delivered peptide from PLGA depots, leuprolide acetate, used to suppress testosterone in prostate cancer patients to inhibit growth of the hormone-dependent cancer, was loaded in SM PLGA microspheres employing an ionic affinity trap, $ZnCO_3$, to create pores for self-encapsulation and to facilitate continuous release of peptide. The resulting SM microspheres (FIG. 5) encapsulated 3.0±0.2% (w/w peptide/polymer matrix) leuprolide acetate (5 measurements) and released the peptide in vitro slowly and continuously for 2 months (FIG. 2B). After administration of a single injection of the same formulation in rats, slow release of leuprolide acetate was observed, as indicated by the steady suppression of testosterone (FIG. 2C) (owing to down-regulation of LHRH receptors) before escaping castration levels after 6-weeks. Similar behavior was observed after two injections of the 1-month Lupron Depot™ formulation, whereas both negative control groups, leuprolide acetate-free SM-microspheres and a 1-month dose of solution leuprolide, were ineffective to suppress testosterone. Model proteins, bovine serum albumin and lysozyme, were also slowly released, albeit in a first-order fashion (FIG. 6), without any signs of classic acid-induced aggregation of BSA and with full monomeric and enzymatic activity recovery of lysozyme in the polymer after 1-month release incubation. Note that in this example, the leuprolide does not freely diffuse across the polymer phase (which does not have acidic end groups), and thus the peptide likely distributes to the polymer pores during encapsulation.

Ultimate success of microencapsulation of expensive biotech drugs requires minimal drug losses during encapsulation. In a single batch process with SM microspheres, the percentage of drug from the loading solution retained within the final particles, i.e., the encapsulation efficiency (EE), is low (~1.5-13%) by the passive process. However, as with minimal or no peptide or protein damage occurs upon self-microencapsulation, the loading solution could be reasonably recycled multiple times with concentration adjustment. A similar issue was resolved in the marketed Doxil™ stealth liposomes by the active loading of doxorubicin via precipitating the drug with ammonium sulfate as it diffused into the empty liposome.

We investigated active loading strategies using two vaccine antigens (ovalbumin (OVA) and tetanus toxoid (TT)). For example, OVA or TT protein antigens were loaded into SM PLGA containing, as an ionic affinity trap, lyophilization-stabilized $Al(OH)_3$ adjuvant (ASM, Table 1), which absorbed the antigen into the polymer matrix from surrounding 0.5 or 0.8 or 1 mg/mL antigen solution, with 98±1% EE (6 measurements) and 1.0±0.05% OVA loading (6 measurements) (ASM-3, tables S3 and S4) or 87±0.4% EE (3 measurements) and 1.6±0.03% TT loading (Table 5). Extent of self-healing of polymer pores was also easily enhanced at 37° C. in the active-loading microspheres by addition of a plasticizer, diethyl phthalate (DEP), to the polymer to further mobilize the hydrated polymer chains (FIG. 7). After self-microencapsulation, decreased surfaces pores are visible with plasticizer added (FIG. 3A and B). Vaccine antigens were effectively self-encapsulated with the active loading strategy in both preparations, as indicated by slow-release of the antigens relative to unencapsulated $Al(OH)_3$ in 190 mM sodium citrate (FIG. 8), phosphate buffered saline (PBS) (FIG. 3C), and PBS+0.02% Tween® 80+0.2% BSA (FIG. 3D). Hence, it is now possible to self-microencapsulate in biodegradable polymers the entire mass of bioactive macromolecules from a low concentration aqueous solution by simple mixing and heating of the solution with an SM-polymer matrix. Also noteworthy were a) the absent requirement of a drying step after microencapsulation of OVA and TT, as drying can cause irreversible damage to proteins, and b) the complete release of antigenically active TT without any apparent common formaldehyde or acid-induced antigen instability.

Spontaneous self-healing in homogenous polymer systems has been described in nano-scale cracks of solid rocket propellants, following bullet holes in plastic plates, film formation from latex particles, and across lap joints of polymer films. The process mechanism, which has found to be ubiquitous to polymers in the vicinity of their $T_g$ or above has been analyzed in detail to involve multiple elements such as: a) polymer chain interdiffusion, b) minimization of energetically unfavorable interfacial area, and c) transfer of energy stored in a defect. We first observed spontaneous pore closing in PLGA microspheres that encapsulated a water-soluble polypeptide during the initial burst release of peptide less than 24 hours after exposure of the polymer to aqueous media at physiological temperature; the resulting closure of the peptide release route initiated a lag phase in release characteristic of this polymer when above a critical MW. Initial studies thereafter to demonstrate the self-encapsulation paradigm in aqueous media attempted to obtain high loading with low initial burst (as seen in FIG. 1F) suffered from poor interconnected networks or pore networks which would not close (likely due to very high porosity of the polymer). We found that polymer matrices with moderate porosity and defects ~2 μm of less (FIG. 1B) could be healed in aqueous solution when pores were created by sugar or salt similarly as those observed during the initial peptide release. Consistent with previous mechanistic analysis, self-encapsulation requires a minimum temperature for polymer-chain mobility to occur over reasonable time scales (FIG. 1F).

The benefits and uses of the self-microencapsulating paradigm are far reaching. For example, a clinician can mix sterile SM micro spheres with an injectable solution of vaccine (e.g., tetanus toxoid) before injecting into women of child-bearing age, providing improved immunity for their unborn children against neonatal infection. New biomaterial architectures (e.g., drug-eluting stent coatings) that release process-sensitive large molecules as previously unchartered formulation conditions (e.g., high temperature, reactive molecules, organic solvent) can be used to create the SM polymer delivery system without concern of damaging the encapsulated macromolecule. For manufacturing, a mixture of several different SM micro sphere formulations, each having distinct design characteristics (release kinetics, size, surface biofunctional groups) can be combined for a drug of interest in a single sterile mixing step. With the absence of aseptic processing of organic solvents, this paradigm can have significant cost savings, which was a critical factor in halting production of the Nutropin Depot, the first and only FDA approved injectable protein depot. The simplicity of self-microencapsulation can also significantly facilitate various controlled release approaches, providing more rapid advancement of controlled release products and technology.

The following materials and methods were employed to demonstrate the present technology.

Materials: Poly(D,L-lactic-co-glycolic acid) (PLGA) 50:50 with an i.v. =0.20 dl/g in hexaflouro isopropanol at 30° C. (Lot # A07-044, end-group=1-dodecyl ester, weight average molecular weight ($M_w$)=11 kDa) of Lactel Absorbable Polymers was purchased from DURECT Corporation (Cupertino, Calif., USA). PLGA 50:50 with an i.v.=0.19 dl/g in chloroform at 30° C. (Lot # 1158-515, end-group=methyl ester, $M_w$=19 kDa) and 0.57 dug in hexafluoroisopropanol at 30° C. (Lot # W3066-603, end-group=lauryl ester, $M_w$=51 kDa) were purchased from Lakeshore Biomaterials (Birmingham, Ala., USA). a,a-Trehalose dihydrate was purchased from Pfanstiehl (Waukegon, Ill., USA), zinc carbonate ($ZnCO_3$) was from ICN Biomedicals Inc., and 7-methoxycoumarin-3-carbonyl azide was from Invitrogen Corporation (Carlsbad, Calif., USA). Tetrahydrofuron (THF) was purchased from Fisher-Scientific (Pittsburgh, Pa., USA). Tetramethyl-rhodamine (TMR)-dextran was purchased from Invitrogen Corporation (Carlsbad, Calif., USA). Tetanus toxoid (TT) (3120 Lf/mL) and equine tetanus antitoxin were received as gift samples respectively from Serum Institute of India Ltd. (Pune, India) and U.S. Food and Drug Administration (Silver Spring, USA). Human tetanus immune globulin (HyperTET™ S/D, 250 units) was purchased from Talecris Biotherapeutics, Inc. (Research Triangle Park, N.C., USA). Poly(vinyl alcohol) (PVA) (9-10 kDa, 80% mol hydrolyzed), Alhydrogel™ aluminum hydroxide adjuvant gel ($Al(OH)_3$), bovine serum albumin (BSA) fraction V, ovalbumin (OVA), lysozyme from chicken egg white, sodium hydroxide (NaOH), magnesium carbonate ($MgCO_3$), BSA labeled with fluorescein isothiocyanate (BSA-FITC), sodium citrate, p-nitrophenyl phosphate liquid substrate, and phthaldialdehyde reagent (containing 1 mg o-phthaldialdehyde per mL solution of 2-mercaptoethanol as the sulfhydryl moiety) were purchased from Sigma-Aldrich (St. Louis, Mo., USA). Leuprolide acetate (Batch #091203) was purchased from Shanghai Shjnj Modern Pharmaceutical Technology Co., Ltd (Shanghai, China). Male Sprague-Dawley rats were procured from Charles River Laboratories. Isoflurane was purchased from Baxter Healthcare Corporation (Deerfield, Ill., USA). B-D Microtainer™ blood collection and serum separation tubes were purchased from Becton, Dickinson and Company (Franklin Lakes, N.J., USA). Goat anti-human IgG-alkaline phosphatase was purchased from Jackson ImmunoResearch Laboratories, Inc. (West Grove, Pa., USA). All other common salts, reagents, and solvents were purchased from Sigma-Aldrich. Size exclusion-high performance liquid chromatography (SE-HPLC) columns (TSK gel G3000SWx1 and TSK gel G2000SWx1 columns, Tosoh Biosciences LLC, Montgomeryville, Pa., USA), Shodex Protein KW-G size exclusion chromatography guard column (Showa Denko, N.Y., USA), Nova-Pak C18 column (4 μm, 3.9×150 mm) and Bonda-Pak C18 guard column (4 μm) (Waters Corporation, Milford, Mass., USA) were used.

Conjugating BSA to a pH-insensitive fluorescent coumarin: About 1.2 g BSA was dissolved in 40 mL of 0.2 M sodium bicarbonate (pH 4.5). To this, 2 mL of 10 mg/mL 7-methoxycoumarin-3-carbonyl azide in dimethyl sulfoxide (DMSO) was added while stirring. The solution was stirred continuously at room temperature in darkness for 90 min. To quench the reaction, 4 mL of 1.5 M hydroxylamine hydrochloride was added and then the solution was extensively dialyzed using a 25,000 Da $M_w$ cut-off membrane against degassed distilled water at 4° C.

Preparation of self-microencapsulating (SM) PLGA microspheres: Various formulations of self-microencapsulating PLGA 50:50 ($M_w$=11, 51, and 19 kDa) microspheres (Table 1) were prepared by a double emulsion (water-in-oil-in-water (W/O/W))-solvent evaporation method without drug. Briefly, polymer solutions of various PLGAs were first prepared by dissolving the required amount of polymer in 1 mL methylene chloride ($CH_2Cl_2$) in a 5- or 10-mL syringe or 10-mL glass tube. Suitable initial water phase (WP) was added to the corresponding polymer solution and immediately homogenized as per the first homogenization conditions specified in Table 1 using a Tempest $1Q^2$ homogenizer (The VirTis Company, Gardiner, N.Y., USA) equipped with a 10 mm shaft in an ice water bath to create the respective first emulsion. Two mL of aqueous 5% PVA was added to the first emulsion of all the formulations, vortexed or homogenized as per the second homogenization/vortexing conditions (Table 1), and the resulting emulsion was injected into 100 mL of chilled (ASM microspheres) or non-chilled (TM-1 and SM-1 to SM-5 microspheres) 0.5% PVA solution under continuous stirring. Microspheres were stirred 3 h at room temperature, and collected with sieves to separate by size (20-63 and 63-90 μm) and washed thoroughly with distilled water to help remove residual PVA. Collected SM PLGA microspheres were then freeze-dried using a freeze drier (Labconco Corporation, Kansas City, Mo., USA) and stored at −20° C. until further use.

TABLE 1

Formulation conditions for preparing traditional (lysozyme encapsulated) and various types of SM PLGA 50:50 microspheres.

| Formulation code | Initial water phase (WP) composition | PLGA 50:50 | | WP volume (μL) | First homog. | Second homog./ vortexing |
| --- | --- | --- | --- | --- | --- | --- |
| | | $M_w$ (kDa) | Conc.(mg polymer in 1 mL $CH_2Cl_2$) + excipient | | | |
| SM-1 | 500 mg trehalose in 1 g PBS | 51 | 320 | 175 | 20,000 rpm for 1.5 min | Homog. at 6000 rpm for 45 s |
| SM-2 | 300 mg/mL BSA in PBS | 19 | 700 | 150 | 10,000 rpm for 1 min | Vortexing for 15 s |
| SM-3 | 0 or 500 mg trehalose in 1 g PBS | 51 | 320 + 0, 4.8, 14.4, and 39.5 mg $MgCO_3$ | 25, 100, 200, and 350 | 17,000 rpm for 1 min | Homog. at 6000 rpm for 25 s |
| SM-4 | 500 mg trehalose in 1 g PBS | 11 | 1100 | 175 | 20,000 rpm for 1.5 min | Homog. at 6000 rpm for 45 s |
| TM-1 | 200 mg/mL lysozyme with or without 0.45M sucrose in water | 51 | 320 | 110 | 20,000 rpm for 1.5 min | Homog. at 6000 rpm for 45 s |
| SM-5 | 1 g PBS or 500 mg trehalose in 1 g PBS | 51 | 320 + 0, 3.5, and 10 mg $ZnCO_3$ | 200 | 10,000 rpm for 1 min | Vortexing for 15 s |
| ASM | 300 μL of 25 mM succinate buffer (pH 4.0) containing 13.1-13.8 mg $Al(OH)_3$ gel and 14.1-15 mg trehalose | 51 | 250 + 0, 7, and 14.2 mg DEP | 200 | 17,000 rpm for 1 min | Vortexing for 50 s |

SM: self-microencapsulating PLGA microsphere formulation;
TM: traditional PLGA microsphere formulation;
ASM: active self-microencapsulating PLGA microsphere formulation;
$CH_2Cl_2$: methylene chloride;
$M_w$: molecular weight;
PBS: phosphate buffered saline (pH 7.4);
$MgCO_3$: magnesium carbonate;
$ZnCO_3$: zinc carbonate;
DEP: diethyl phthalate;
Conc.: concentration

TABLE 2

Conditions for investigating passive and active self-microencapsulation
of enzyme/protein/peptide by various types of PLGA 50:50 SM microspheres.

| FC | Enzyme/protein/peptide self-encapsulated | SM microspheres added (mg) | Concentration of loading solution:volume (mg/mL:mL) | Incubation temperature/duration (° C./h) | |
|---|---|---|---|---|---|
| | | | | Loading | Self-healing |
| SM-1 | Lysozyme | 200 or 225 | 200 or 230:1 or 1.4 | 4/48 | 42.5/44 |
| SM-2 | BSA-coumarin | 125 | 43 or 79 or 115 or 157 or 175 or 204: 0.8 or 1 | 4/24 or 48 | 37 or 42/18 or 24 |
| SM-3 | BSA or Lysozyme or TMR-Dextran or FITC-Dextran | 50 or 100 (FITC-Dextran/ TMR-Dextran) or 80 or 150 (BSA/ Lysozyme) | 1 (TMR-Dextran or FITC-Dextran) or 65 (FITC-Dextran) or 200 or 300 (BSA or Lysozyme with or without 0.45M sucrose):1 | 4/24 or 48 (TMR-Dextran or FITC-Dextran) or 4/16 or 72 (BSA or Lysozyme) | 42.5/48 or 72 (TMR-Dextran or FITC-Dextran) or 43/46 or 48 (BSA or Lysozyme) |
| SM-4 | Lysozyme | 200 | 250 with or without 0.45M sucrose:1 | 4/24 | 37/12 |
| SM-5 | Leuprolide acetate | 1000 | 127:4 | 4/42 | 43/48 |
| ASM | OVA or TT | 20 | 0.5 or 1.0:0.4 (OVA) or 0.8:0.5 (TT) | 10/48 (OVA) or 24 (TT) + 25/24 (OVA and TT) | 37/30 (OVA) or 38/40 (TT) |

FC: formulation code;
SM: self-microencapsulating PLGA microsphere formulation;
ASM: active self-microencapsulating PLGA microsphere formulation;
OVA: ovalbumin;
TT: tetanus toxoid.

Passive and active self-healing microencapsulation of large molecules (lysozyme, BSA, leuprolide, OVA and TT) by PLGA Microspheres: The passive self-microencapsulation paradigm was studied using all the microspheres formulations given in Table 1, except Al(OH)$_3$-encapsulated PLGA microspheres, which were used for testing active self-microencapsulation of OVA and TT. Briefly, microspheres of 20-63 μm size were incubated with chilled (4° C.) enzyme/protein/peptide solution on a rocking platform (VWR Scientific, West Chester, Pa., USA) at 4° C. (loading conditions) for a specified period of time, as listed in Table 2. After completion of loading duration, microspheres were then transferred on a rigged rotator (Glas-Col, Terre Haute, IN, USA) to prevent interparticle healing in an incubator maintained at specified temperature for specified duration (self-healing conditions), as listed in Table 2. Microspheres were then removed, washed 10 times with distilled and deionized water (ddH$_2$O), centrifuged at 3000-3800 rpm for 5-10 min, and freeze-dried. To test active self-microencapsulation, about 21 mg Al(OH)$_3$-encapsulated PLGA microspheres of 20-63 μm size were incubated with low protein (OVA or TT) concentration solution (0.5-1.0 mg/mL, volume=0.4 or 0.5 mL) on a rigged rotator for a specified duration at 10 and 25° C. for active protein loading and then at 37 or 38° C. for self-healing (Table 2). Microspheres were then removed, washed one time with ddH$_2$O, centrifuged with conditions given above and supernatant was removed. Microspheres were used without drying.

Preparation of lysozyme encapsulated PLGA microspheres by a traditional encapsulation (TE) method: As summarized in Table 1, one hundred ten μL of 200 mg/mL aqueous lysozyme solution with or without 0.45 M sucrose was added to 320 mg PLGA (50:50, M$_w$=51 kDa) in 1 mL CH$_2$Cl$_2$ and immediately homogenized in a 5-mL-syringe at 20,000 rpm for 1.5 min, creating the first emulsion. Two mL of 5% PVA was immediately added to the tube and the mixture was then homogenized for 45 s at 6,000 rpm and the resultant emulsion was injected into 100 mL of 0.5% PVA under continuous stirring. Microspheres were stirred for 3 h at room temperature, and collected with sieves to separate by size (20-63 and 63-90 μm) and washed thoroughly with ddH$_2$O to help remove residual PVA.

Coomassie (modified Bradford) protein assay: A modified Bradford assay was used to determine protein concentrations. Briefly, appropriate volume of standard or sample was mixed with Coomassie Plus™ reagent (Thermo Fisher Scientific, Rockford, Ill., USA) in a 96-well plate (Nalge Nunc International, Rochester, N.Y., USA). Then, the absorbance was read at 595 nm within 30 min using a Dynex II MRX microplate reader (Dynex Technology Inc., Chantilly, Va., USA).

Size exclusion-high performance liquid chromatography (SE-HPLC) analysis of protein: Samples were injected into the TSK Gel G3000SW (lysozyme, BSA and BSA-Coumarin) or G2000 SW (OVA) column (7.8 mm i.d.×30 cm long) column (Tosoh Biosciences LLC, Montgomeryville, Pa., USA) attached with a Shodex™ Protein KW-G guard column (Showa Denko, N.Y., USA), eluted by 0.05 M potassium phosphate containing 0.2 M NaCl (pH 7.0) for (lysozyme and OVA) or PBS (pH 7.4) for (BSA and BSA-Coumarin) at a flow rate of 0.9 for (lysozyme, BSA and BSA-Coumarin) or 0.7 (OVA) mL/min. UV detection at 215 and 280 nm and fluorescence detection with excitation and emission wavelengths of 278 nm and 350 nm for BSA, OVA and lysozyme, and 384 nm and 480 nm for BSA-Coumarin were used.

High performance liquid chromatography (HPLC) analysis of leuprolide acetate: Analysis of leuprolide acetate was accomplished by HPLC, with a gradient of acetonitrile (Solvent A) and 0.05 M sodium phosphate buffer, pH 7.0 (Solvent B) on a Nova-Pak C18 column (4 μm, 3.9×150 mm, Waters Corporation, Milford, Mass., USA). The gradient method was 0 min (20% A), 6 min (30% A), 9.5 min (37% A), 11.5 min (37% A), 16.5 min (50% A), and 19 min (20%

A), followed by a 2 min recovery. UV detection was measured at 215 nm and 280 nm, and fluorescence detection was performed at excitation and emission wavelengths of 278 and 350 nm, respectively.

Determination of active loading by protein disappearance from the loading solution: To follow active loading (i.e., mass fraction of encapsulated species in PLGA) as a function of time and temperature of incubation, after various stages of the incubation, the protein/active SM (Al(OH)$_3$-encapsulated) PLGA microsphere mixtures were passed through a low protein binding PVDF membrane filter (Millipore, Bedford, Mass., USA) and remaining protein (OVA or TT) in solution was analyzed by the modified Bradford assay.

Determination of loading by polymer removal and recovery of residual protein/peptide: For determination of soluble lysozyme, BSA, and BSA-Coumarin, PLGA microspheres were dissolved in acetone and dispersed for 1 h, centrifuged at 13,000 rpm for 10 min and the supernatant was removed. Centrifugation/supernatant removal was repeated 3-fold, and the residual solvent was removed via concentrator (Vacufuge™ concentrator 5301 (Eppendorf International, Hamburg, Germany)). The remaining protein was then dissolved in 10 mM potassium phosphate buffer, pH 7.0 (lysozyme) or PBS, pH 7.4 (BSA and BSA-Coumarin) and analyzed by SE-HPLC.

Leuprolide acetate content in self-encapsulated PLGA micro spheres was determined by two-phase extraction. Briefly, about 5 mg leuprolide acetate self-encapsulated PLGA microspheres (n=5) were weighed into 5-mL glass vials. To these vials, 1 mL of methylene chloride and 2 mL of 50 mM sodium acetate (pH 4.0) were added, followed by vortexing for 1 min. One and a half mL of buffer layer was removed, replaced with 1.5 mL of same buffer (2 extractions) or 50 mM sodium acetate+1 M NaCl (3 extractions) and extracted. The content of leuprolide acetate in each extracted fraction was then analyzed and quantified by HPLC. Five extractions were found to be sufficient to remove leuprolide completely from PLGA microspheres as the HPLC peak of leuprolide acetate disappeared by the 6$^{th}$ extraction.

To determine the OVA content in active self-encapsulated PLGA microspheres, microspheres were dissolved in ethyl acetate and centrifuged at 6,000 rpm for 5 min. The supernatant polymer solution was removed and the aluminum hydroxide-OVA sediment was washed twice with ethyl acetate. The sediment was then dried at 30° C. using the Vacufuge™ to remove ethyl acetate. One milliliter of 190 mM sodium citrate solution was added to the dried aluminum hydroxide-OVA pellet, mixed thoroughly, and incubated at 37° C. for 3 days with constant agitation. In control studies, this duration was determined to be sufficient for complete elution of OVA from the aluminum hydroxide gel. Then, the samples were centrifuged at 6,000 rpm for 5 min and soluble OVA amount in supernatant was analyzed by the SE-HPLC. To the remaining residue, a reducing and denaturing solution (10 mM dl-dithiothreitol+6 M urea+1 mM EDTA) was added to dissolve any aggregate and centrifuged. The content of insoluble aggregate of OVA in supernatant was analyzed by the modified Bradford assay (S1).

Enzyme-linked immunosorbent assay (ELISA): Antigenically active TT was determined by the ELISA. Except for final incubation step with p-nitrophenyl phosphate liquid substrate, all initial ELISA steps were performed at room temperature. Briefly, 100 μL of 2-3 international units (IU)/mL of equine tetanus antitoxin in PBS (pH 7.2) was added to 96-well microtitration plates (Nalge Nunc International, Rochester, N.Y., USA) and incubated overnight. The plates were washed 3-5 times between all steps with PBS containing 0.05% Tween™ 20 (pH 7.2). Phosphate blocking buffer (PBB, PBS/0.5% BSA/0.05% Brij™ 35, pH 7.4) was used as a diluent for all TT samples and antibodies (except equine tetanus antitoxin above). Standard TT with known concentration and test samples were diluted at 2-fold steps in coated plates using PBB as a diluent. The plates were held for 2 h and washed. Then, 100 μL of human anti-TT IgG (Hyper-TET™ S/D, 1:5000 dilution) was added and allowed to react for 2 h followed by 100 μL of goat anti-human IgG-alkaline phosphatase diluted 1:20000 in PBB for another 2 h. The plates were washed and 100 μl of p-nitrophenyl phosphate liquid substrate was added. After 30 min incubation at 37° C., the absorbance was read at 405 nm on a Dynex II MRX microplate reader (Dynex Technology Inc., Chantilly, Va., USA) equipped with Revelation 4.21 Software. Log/Logit curve fitting model was used to plot the standard curve and calculate unknown concentration of TT in test samples.

Evaluation of in vitro release of protein and peptide from SM and TE PLGA microspheres: In vitro release of large molecules from passive and active self-encapsulated PLGA microspheres was determined by quantifying either the amount released into the release medium (BSA, lysozyme, TT, and OVA) or the amount of encapsulated species directly remaining in the polymer (leuprolide acetate). Briefly, ~4-10 (passive BSA/lysozyme/leuprolide acetate SM PLGA microspheres) or 20 (active OVA or TT self-encapsulated Al(OH)$_3$-PLGA microspheres) mg of microspheres were incubated in either 0.5-1.5 mL of phosphate buffered saline (PBS)+0.02% Tween 80 (PBST) (pH 7.4) or both PBS and 190 mM sodium citrate (active OVA self-encapsulated Al(OH)$_3$-PLGA microspheres) or PBST+0.2% BSA (active TT self-encapsulated Al(OH)$_3$-PLGA microspheres) at 37° C. under constant agitation (100 rpm/min). Release medium was removed and replaced with fresh buffer at pre-selected time points. Soluble BSA/OVA/lysozyme in release media was quantified by SE-HPLC and modified Bradford protein assay. Release of antigenic TT was determined by ELISA. In order to determine the in vitro release of leuprolide acetate, peptide remaining in the polymer after incubation of specified period was determined by the method described in the loading analysis. Cumulative amount of peptide released was then calculated by subtracting the remaining amount of peptide in the polymer from initial peptide content (S2).

Determination of soluble and insoluble lysozyme loading by amino acid analysis (AAA): Determination of total and soluble lysozyme content in microspheres and soluble lysozyme content in other solution-based samples was performed by AAA. Briefly, microspheres (~4 mg), soluble protein solutions, and standard samples were weighed into clear glass ampoules in a total volume of 1.5 ml 6 N HCl. Ampoules were then sealed under light vacuum and incubated at 110° C. for 25 h. The hydrolyzate from each vial was completely emptied into microcentrifuge tubes and each vial was rinsed with 250 μL water and emptied into respective microcentrifuge tube. The resulting solution was then evaporated under vacuum at room temperature. About 1 mL of 1.0 M sodium bicarbonate buffer (pH 9.5) was weighed into each tube to neutralize the remaining acid. For individual amino acid analysis, a weighed amount of 350 μL of hydrolyzed protein solution and 350 μL of o-phthaldialdehyde reagent solution were combined in a microcentrifuge tube, vortexed for 15 s, and immediately injected onto a C18 column fitted with a guard column (total time from mixing to injection <1 min), using a previously reported HPLC method for AAA with o-phthaldialdehyde reagent (S3).

Samples were eluted (gradient elution) with mobile phases of methanol:water (65:35) (A) and methanol:THF:50 mM phosphoric acid (20:20:960) (titrated to pH 7.5 with 10 N NaOH) (B) at a flow rate of 1.4 mL/min. Gradient elution conditions were 40% A for 0.5 min, 17 min concave gradient to 50% A, 15 min linear gradient to 100% A, 5 min isocratic elution with 100% A, 7.5 min linear gradient to 40% A, and isocratic 40% A for 5 min. Amino acids were detected by measuring fluorescence respectively at an excitation and emission wavelength of 350 and 455 nm. Protein and standards were quantified using the average of the 3 individual amino acids standards found to be stable under hydrolysis conditions: alanine, phenylalanine, and lysine.

Scanning electron microscopy (SEM): Surface morphology of microspheres was examined by taking SEM images using a Hitachi S3200N scanning electron microscope (Hitachi, Tokyo, Japan). Briefly, microspheres were fixed previously on a brass stub using double-sided adhesive tape and then were made electrically conductive by coating, in a vacuum, with a thin layer of gold (approximately 3 to 5 nm) for 60 s at 40 W. The surface view images of microspheres were taken at an excitation voltage of 5-10 kV.

Confocal microscopy: Distribution of self-microencapsulated protein in the PLGA microspheres was observed by taking confocal images of BSA-coumarin loaded PLGA microspheres. Briefly, 1 mg of BSA-coumarin loaded PLGA microspheres were suspended in 80 µL of water. A droplet of this suspension was placed on a clean glass slide, a glass cover slip placed on top of the droplet, and excess of water was removed. Samples were imaged at an excitation/emission wavelength of 384/480 nm using a confocal microscope (Olympus America Inc., Center Valley, Pa., USA).

Determination of polymer matrix porosity of SM microencapsulating microspheres: Measurement of polymer matrix porosity of blank SM microencapsulating PLGA microspheres was done by Porous Materials, Inc. (Ithaca, N.Y., USA) using an AMP-60K-A-1 mercury porosimeter, generating pore volume versus pressure data. The pore volume was reported as volume per gram microspheres (cc/g). Total microsphere volume was calculated as the sum of the pore volume and the polymer volume, where the polymer density (1.25 g/cc for 51 kDa PLGA 50:50, provided by manufacturer) and weight of the porosimetry sample were used to calculate the pore volume. Percent porosity was calculated as the pore volume per total microsphere volume. Pressure associated with microspheres' packing and surface wetting, before mercury intrusion into the pores had taken place, was not calculated into the final pore volume as has been reported previously (S4). The method of determination of porosity utilized large amount of microspheres sample (~250 mg) and there was no significant difference (p>0.05) among the different measurements (three measurements) of the same formulation. Hence, only one test was run for the measurement of polymer matrix porosity of various SM microspheres formulations.

Kinetics of self-healing microencapsulation: About 50 mg of SM PLGA 50:50 ($M_w$=51 kDa) microspheres were placed into separate tubes of 65 mg/mL dextran-FITC (10,000 $M_w$). Microspheres were incubated at 4° C. for 20 h, and then transferred to 42.5° C. for 72 h, with approximately 10% of microspheres removed at preset time points while replacing the volume post sampling with fresh dextran-FITC solutions. Sample microspheres were washed 10-fold with distilled water, with centrifugation at 3200 rpm for 10 min to collect the microspheres after each wash. The dextran-FITC was extracted using acetone to dissolve the PLGA and concentrating the insoluble dextran-FITC using centrifugation (10,000 rpm at 10 min), and repeating 3-fold. Dextran-FITC was dissolved in PBS, pH 7.4, and loading was determined via HPLC with fluorescence (without column seperation) using 20 or 40 µL injection volume and a 1 mL/min PBS, pH 7.4 mobile phase. The fluorescence of the dextran-FITC was measured respectively at an excitation and emission wavelength of 490 and 520 nm.

Evaluation of testosterone suppression in rats following injection of leuprolide acetate self-encapsulated PLGA microspheres: The ability of PLGA self-healing microencapsulation to provide long-term in vivo release was evaluated by assessing long-term testosterone suppression after a single injection of leuprolide acetate self-encapsulated PLGA microspheres in male Sprague-Dawley rats (S5-S8). The treatment of experimental animals was in accordance with University committee on use and care of animals (University of Michigan UCUCA), and all NIH guidelines for the care and use of laboratory animals. Male Sprague-Dawley rats of 6 weeks old were housed in cages and given free access to standard laboratory food and water, and allowed one week to acclimate prior to study initiation. Animals were anesthetized with 2-4% isoflurane administered by a calibrated vaporizer (Midmark, Orchard Park, N.Y., USA). The leuprolide acetate self-encapsulated PLGA microspheres (1×2-month dose), leuprolide acetate solution (1×1-month dose), and blank SM PLGA microspheres without drug (1× dose) in a liquid vehicle (1% w/v carboxymethylcellulose and 2% w/v mannitol), and commercial 1-month Lupron Depot (Abbott Laboratories, North Chicago, Ill., USA) (2× dosing at days 0 and 28) were subcutaneously injected at the back (lower neck portion) of rats (6 animals/study group). Total dose of leuprolide acetate was based on 100 µg/kg/day. Animal body weight considered for dosing leuprolide acetate was 425 g which is projected body weight of male Sprague Dawley rat at midpoint (day 28) of the study (as per the weight (g)/age (weeks) curve given by Charles River Laboratories). Blood samples were collected via jugular vein stick before (day -7 and 0 for baseline testosterone level) and after (1, 7, 14, 21, 28, 35, 42, 49, and 56 days) injection of preparations. The collected blood samples were immediately transferred to B-D Microtainer™ blood collection and serum separation tubes previously incubated in ice, centrifuged at 8,000 rpm for 10 min, and then the serum was removed and stored in microcentrifuge tubes at −20° C. until further use. Serum testosterone levels were assayed by radioimmunoassay using a TESTOSTERONE Double Antibody-125I RIA Kit (MP Biomedicals LLC., Solon, Ohio, USA) at the University of Pennsylvania Diabetes Center (Philadelphia, Pa., USA). Lowest detection limit of testosterone was 0.1 ng/mL. In case of samples which exhibited testosterone level below the detection limit, a 0.1 ng/mL value was used for statistical evaluation and plotting the curve.

Sterilization of active SM (Al(OH)$_3$-PLGA) PLGA microspheres with gamma irradiation: Active SM PLGA micro spheres were irradiated by using $^{60}$Co as irradiation source (Michigan Memorial Phoenix Project, University of Michigan) at 2.5 MRad dose and 0.37 MRad/h dose rate. Briefly, about 250 mg active SM PLGA microspheres were freeze-dried, placed in 5-mL ampoules and then ampoules were sealed under vacuum. All the samples were irradiated at room temperature.

Statistical Analysis: The results are expressed as mean±standard error of mean (n=3 or 5 or 6). An unpaired Student's t-test was used to assess statistical significance between numerous SM PLGA micro sphere formulations with respect to polymer porosity, protein and peptide loading, stability, and in vitro release, and in vivo testosterone level. Results were considered statistically significant if $p<0.05$.

Goodness of self-encapsulation—Effect of pore-forming excipients/initial water phase volume on lysozyme loading and initial burst release: The goodness of self-encapsulation in PLGA microspheres as indicated by elevated lysozyme loading (open bar chart) and minimal initial burst (closed bar chart) of enzyme employing diversity of pore-forming excipients/initial water phase volume to create the PLGA 50/50 pore network is shown in FIG. 4.

Limitations on molecular size—Self-microencapsulation of dextran blue: As suggested by the open pore distribution in FIG. 1 (before and after loading lysozyme in SM microspheres) very large molecules can penetrate the polymer pore network and become encapsulated. Therefore, we tested the virtual upper limit of molecular size of biomacromolecules by encapsulating TMR-dextran ($M_w$=2 MDa) relative to low molecular weight 4 kDa FITC-dextran in SM-PLGA 50:50 ($M_w$=51 kDa) microspheres (SM-3, Tables 1 and 2). At a constant solution concentration of 1 mg/mL, which is just below the solubility of the TMR-dextran, both dyes were successfully encapsulated at very similar levels as indicated by the following data determined experimentally (five measurements): SM PLGA microspheres self-encapsulated 0.30±0.01 and 0.22±0.01% w/w TMR-dextran and FITC-dextran 4 kDa, respectively.

Self-healing microencapsulation of leuprolide acetate in PLGA 50:50 ($M_w$=51 kDa) microspheres (SM-5, Tables 1 and 2) is shown in FIG. 5.

Protection of protein during microencapsulation—Improved stability of lysozyme through self-microencapsulation: As lysozyme is a common model protein for testing protein damage during microencapsulation, we self-microencapsulated this enzyme and monitored its loading in terms of monomeric, total, and enzymatically active protein content. The stability of lysozyme encapsulated via self-healing microencapsulation (SM-3 and SM-4, Tables 1 and 2) was compared with the enzyme encapsulated via a traditional w/o/w process (TM-1, Tables 1 and 2). Combined soluble and insoluble lysozyme encapsulated was measured via AAA, and the soluble fractions were determined by SE-HPLC.

Addition of sucrose, as a differentially soluble material, either to inner water phase in the double emulsion (TE method) or loading solution (self-microencapsulation method) resulted in reduced lysozyme loading (% w/w lysozyme/polymer matrix). For example, the lysozyme loading into medium $M_w$ PLGA ($M_w$=51 kDa) microspheres prepared by TE with and without sucrose in WP was 0.65±0.01 and 4.86±0.04%, respectively (three measurements). Whereas lysozyme loading into medium $M_w$ PLGA ($M_w$=51 kDa) microspheres by the self-encapsulation technique with and without sucrose in loading solution was 3.39±0.03 and 5.17±0.08%, respectively (three measurements).

The percentage (% w/w) of loaded lysozyme that exists as intact soluble monomer was slightly higher for the self-microencapsulated microsphere (SM-3, Tables 1 and 2) formulations than the TM-1 formulations. In the absence of sucrose, TM-1 and SM PLGA ($M_w$=51 kDa) microspheres had 85±2 and 90±2% intact monomer (three measurements), respectively. In the presence of sucrose in the loading solution, SM PLGA ($M_w$=51 kDa) microspheres had 98±2% of the loaded protein as intact monomer (three measurements). Importantly, the fraction of total lysozyme loaded as insoluble aggregates was significantly less ($p<0.05$) for self-microencapsulation technique when compared to TE method. For example, lysozyme loaded via TE method (TM-1, Tables 1 and 2) underwent 40±4% and 12±2% insoluble aggregation (three measurements) with or without sucrose in the inner water phase, respectively (FIG. 2F and E). By contrast, the self-microencapsulation technique respectively showed 8±3 and 1±2% insoluble aggregation (three measurements) without and with sucrose in loading solution (FIG. 2C and D) for the SM PLGA ($M_w$=51 kDa) microsphere formulation (SM-3, Tables 1 and 2).

Protection of protein (BSA and lysozyme) against acid-induced protein instability during release from self-encapsulated PLGA microspheres: The success of controlled protein delivery vehicles based on PLGA significantly depends upon the ability of the polymer to retain and release the stable form of proteins under physiological conditions over extended release times. Co-encapsulation of $MgCO_3$ along with proteins in PLGA 50:50 by the TE method has been used to stabilize proteins against the acidic polymer microclimate and released the proteins in a stable form compared to control formulations without an ionic affinity trap. As BSA is a common model protein for assessing protein damage due to acid produced by the PLGA polyester during long-term controlled release, we self-microencapsulated the protein into SM-PLGA 50:50 microspheres containing $MgCO_3$ as an acid-neutralizer and porosigen with and without trehalose as an additional porosigen (SM-3, Tables 1 and 2) and monitored its loading, release from microspheres and acid-induced aggregated protein content in the polymer. Blank SM PLGA 50:50 ($M_w$=51 kDa) microspheres containing 3 and 4.5% w/w ($MgCO_3$/polymer matrix) $MgCO_3$ self-microencapsulated 4.25±0.05 and 5.65±0.06% w/w (protein/polymer matrix), respectively (three measurements). Both the self-microencapsulated formulations exhibited a high initial burst (49-54% BSA release after 1-day), which was then substantially reduced by co-encapsulation of trehalose along with $MgCO_3$ during the preparation of SM microspheres (FIG. 6A). Importantly, analysis of the remaining protein in the microspheres after 28 days of in vitro release provided a mass balance (total recovery) between 109±4 to 121±2% (three measurements) and out of which <2% BSA was aggregated.

Another model protein, lysozyme, was similarly self-encapsulated in blank PLGA 50:50 ($M_w$=51 kDa) microspheres (SM-3, Tables 1 and 2) containing 0, 1.5, 4.3, 11.0% w/w ($MgCO_3$/polymer matrix). The amount of lysozyme self-encapsulated in 0, 1.5, 4.3, 11.0% w/w $MgCO_3$ loaded blank PLGA 50:50 microspheres was 4.5±0.2, 6.4±0.1, 9.8±0.3, and 8.7±0.4% w/w (lysozyme/polymer matrix), respectively (three measurements). The release rate of lysozyme from above mentioned formulations was directly related to the amount of ionic affinity trap ($MgCO_3$) loaded into the blank PLGA 50:50 microspheres (FIG. 6B). For example, after 28 days, the cumulative amount of lysozyme released from self-microencapsulated microspheres formulations was 30±1, 41±1, 51±4, and 57±4% respectively for 0, 1.5, 4.3, and 11.0% w/w $MgCO_3$ loaded blank PLGA 50:50 microspheres. The amount of protein remaining in the microspheres after 28 days of release, including soluble monomer, soluble aggregates, and insoluble aggregates, was similarly quantified and >90% mass balance (total recovery) was achieved for all four formulations. For example, total amount of lysozyme recovered from self-microencapsulated microspheres formulations was 92±2, 91±1, 99±4, and 110±4% (three measurements) respectively for 0, 1.5, 4.3, and 11.0% w/w $MgCO_3$ loaded PLGA 50:50 microspheres. Importantly, the total amount of soluble protein, both released over 28 days and recovered as residual soluble monomer, was significantly higher (p<0.05) for 4.3 and 11.0% w/w MgCO$_3$-based self-encapsulated microspheres formulations. For example, total (released+residual) amount of soluble protein recovered for 0, 1.5, 4.3, and 11.0% w/w MgCO$_3$ loaded PLGA 50:50 microspheres was 83±2, 85.0±1, 95±4, and 107±4%, respectively. Furthermore, the specific activity of the residual lysozyme remaining in the self-encapsulated microspheres after 28 days of release was analyzed. The specific activity was calculated based upon the total amount of soluble protein analyzed, both monomer and aggregated. The specific activity, given as the percentage of the specific activity of the native, standard lysozyme was 102±6, 116±19, 100±5, and 97±5% respectively for 0, 1.5, 4.3, and 11.0% w/w MgCO$_3$ loaded PLGA 50:50 microspheres. Thus, the soluble lysozyme retained in the self-microencapsulated microspheres after 28 days of release was still completely active within experimental error for all formulations.

Kinetics of PLGA self-encapsulation: In order to determine the time required for self-healing of PLGA to encapsulate large molecules, SM PLGA microspheres (SM-3, Table 1) were loaded with FITC-dextran (SM-3, Table 2) and the loaded biomacromolecular dye was analyzed at various times before and after initiating self-encapsulation by increasing temperature from 4° C. (T<$T_g$) to 42.5° C. (T>$T_g$). At each time point, microspheres were washed extensively with ddH$_2$O to remove any unencapsulated dye. As shown in FIG. 1F, only background levels of dextran were loaded when at the low temperature for 20 h. However, after increasing temperature to 42° C. (at time 0) loading of two separate, but equivalent, formulations both increased steadily over 12 h reaching a maximal and steady loading value for 72 h. Hence, without any manipulation of the polymer (e.g., by plasticization) self-healing time for this formulation was on the order of 12 h. In addition, loading was completely reproducible for the two identical formulations.

PLGA self-healing microencapsulation provides long-term delivery of bioactive large molecules in vivo—Long-term testosterone suppression in rats after single injection of leuprolide acetate self-encapsulated PLGA microspheres: Leuprolide acetate ($M_w$=1209.6 Da) is commonly used in the treatment of hormone-dependent cancers (e.g., prostate cancer) and gynecologic disorders (e.g., endometriosis and precocious puberty). Commercially available injectable PLGA microsphere-based formulation of leuprolide (Lupron Depot™) is prepared by the traditional (water-in-oil-water) encapsulation method. The ability of PLGA self-healing microencapsulation to provide long-term in vivo release was evaluated by assessing long-term testosterone suppression in male Sprague-Dawley rats (six rats/study group) in comparison with commercial Lupron Depot™ and negative controls (FIG. 2C). The initial serum testosterone level (1-2 ng/mL) increased to ~5 ng/mL after one day of subcutaneous injection of Lupron Depot™, leuprolide self-encapsulated PLGA microspheres and leuprolide solution. This initial elevation is typical to treatment with luteinizing hormone-releasing hormone (LHRH) agonists (e.g., leuprolide acetate) resulting from initial stimulation of pituitary LHRH receptors and increased release of luteinizing hormone (LH), thereby stimulating testicular steroidogenesis and release of gonadotropins. The testosterone levels fell below the castration level (0.5 ng/mL) within a week and remained under that level for 6-7 weeks following a single injection of leuprolide acetate self-encapsulated PLGA microspheres and 8 weeks after two injections (day 0 and 28) of Lupron Depot™. Importantly, there was no significant serum testosterone levels difference (p<0.05) between self-encapsulated PLGA microspheres and commercial Lupron Depot™ over a period of 6 weeks, indicating equivalent potential of new PLGA self-healing microencapsulation paradigm to provide long-term in vivo delivery of peptide drugs. In contrast, leuprolide solution control because of the short serum half-life of the peptide, failed to provide testosterone suppression below the castration level during the whole study duration. However, there was a significant serum testosterone levels difference (p>0.05) between negative controls (blank SM PLGA microspheres and leuprolide solution) and long-term leuprolide delivery vehicles (self-encapsulated PLGA microspheres and commercial Lupron Depot™) over a period of 6-8 weeks.

Active self-microencapsulation of protein with high encapsulation efficiency by Al(OH)$_3$-PLGA microspheres—Effect of hydrophobic plasticizer: The encapsulation efficiency of SM PLGA microspheres by the passive self-encapsulation method is 1.5-13%. In addition, as partitioning of the proteins between polymer pores and external solutions should be close to unity when loading by the passive process, high external protein concentrations (e.g., >~100 mg/mL) were required previously to achieve loading >1%. Therefore, to increase the encapsulation of efficiency of SM PLGA microspheres and to reduce external protein concentration, we added a known protein sorbing ionic affinity trap, Al(OH)$_3$, in SM PLGA microspheres (ASM PLGA microspheres, Table 1) and tested their potential to self-microencapsulate different vaccine antigens (ovalbumin (OVA) and tetanus toxoid (TT)), from low aqueous protein concentrations (0.5 or 0.8 or 1.0 mg/mL) (Tables 2-5).

As shown in Table 3, all the three ASM (ASM-1, ASM-2, and ASM-3) PLGA microspheres sorbed the OVA from surrounding protein solution within the incubation time compared blank porous PLGA microspheres, suggesting active self-microencapsulation of protein by ASM PLGA microspheres. Negative loading values were observed with porous blank (no Al(OH)$_3$) microspheres which can be attributed to the uptake of small amounts of water by the polymer leaving behind more concentrated protein solution.

TABLE 3

OVA mass loss kinetics as a function of incubation time from OVA/active SM Al(OH)$_3$-PLGA 50:50 ($M_w$ = 51 kDa) microspheres mixture.

| Temp. and t | | | Formulation code | | | | | | |
|---|---|---|---|---|---|---|---|---|---|
| | | | Remaining OVA mass in solution$^a$ (μg)* | | | | OVA loaded (μg)* | | |
| ° C. | h | IM$^a$ (μg) | Blank | ASM-1 | ASM-2 | ASM-3 | Blank | ASM-1 | ASM-2 | ASM-3 |
| 10 | 3 | 404 | 415 ± 5 | 325 ± 3 | 317 ± 6 | 319 ± 3 | −11 ± 5 | 79 ± 3 | 87 ± 6 | 85 ± 3 |
| | 6 | 404 | 415 ± 3 | 321 ± 4 | 310 ± 4 | 310 ± 1 | −11 ± 3 | 83 ± 4 | 94 ± 4 | 94 ± 1 |

TABLE 3-continued

OVA mass loss kinetics as a function of incubation time from
OVA/active SM Al(OH)$_3$-PLGA 50:50 ($M_w$ = 51 kDa) microspheres mixture.

| Temp. and t | | IM$^a$ | Formulation code | | | | | | | |
|---|---|---|---|---|---|---|---|---|---|---|
| | | | Remaining OVA mass in solution$^a$ (μg)* | | | | OVA loaded (μg)* | | | |
| °C | h | (μg) | Blank | ASM-1 | ASM-2 | ASM-3 | Blank | ASM-1 | ASM-2 | ASM-3 |
| | 24 | 404 | 416 ± 2 | 315 ± 3 | 300 ± 10 | 301 ± 6 | −12 ± 2 | 89 ± 3 | 104 ± 10 | 103 ± 6 |
| | 48 | 404 | 425 ± 3 | 285 ± 3 | 285 ± 7 | 284 ± 4 | −21 ± 3 | 119 ± 3 | 119 ± 7 | 120 ± 4 |
| 25 + 37 | 24 + 30 | 404 | 419 ± 6 | 203 ± 4 | 212 ± 5 | 197 ± 3 | −15 ± 6 | 201 ± 4 | 192 ± 5 | 208 ± 3 |

Temp and t: incubation temperature (° C.) and duration (h);
IM: initial OVA mass in solution
$^a$volume = 0.4 mL;
*Mean ± SE, n = 6
ASM-1: 3.2% w/w Al(OH)$_3$/3.5% w/w trehalose/0% w/w diethyl phthalate (DEP)/PLGA microspheres
ASM-2: 3.2% w/w Al(OH)$_3$/3.5% w/w trehalose/2.5% w/w DEP/PLGA microspheres
ASM-3: 3.2% w/w Al(OH)$_3$/3.5% w/w trehalose/5% w/w DEP/PLGA microspheres

TABLE 4

OVA loading and self-microencapsulation efficiency of active
SM Al(OH)$_3$-PLGA 50:50 ($M_w$ = 51 kDa) microspheres at different
initial loading concentration.

| FC | Initial OVA mass$^a$ (μg) | Remaining OVA mass$^a$ (μg)* | OVA loaded (μg)* | OVA recovered from polymer (μg)* | Encapsulation efficiency$^b$ (%)* | OVA Loading$^b$ (% w/w)* |
|---|---|---|---|---|---|---|
| ASM-1 | 202.1 | 7.1 ± 2.4 | 195.0 ± 2.4 | 194.1 ± 2.2 | 96.1 ± 1.1 | 1.00 ± 0.01 |
| | 404.1 | 203.2 ± 4.3 | 200.9 ± 4.3 | 197.9 ± 3.1 | 49.0 ± 0.8 | 0.98 ± 0.02 |
| ASM-2 | 202.1 | 4.4 ± 0.4 | 197.7 ± 0.4 | 196.2 ± 0.3 | 97.1 ± 0.2 | 0.97 ± 0.01 |
| | 404.1 | 211.8 ± 5.4 | 192.3 ± 5.4 | 190.5 ± 5.6 | 47.1 ± 1.4 | 0.90 ± 0.03 |
| ASM-3 | 205.7 | 2.5 ± 1.6 | 203.2 ± 1.6 | 202.1 ± 1.3 | 98.3 ± 1.1 | 1.00 ± 0.05 |
| | 404.1 | 196.6 ± 2.7 | 207.5 ± 2.7 | 203.5 ± 3.4 | 50.4 ± 1.7 | 1.00 ± 0.03 |

FC: formulation code;
$^a$volume = 0.4 mL;
*Mean ± SE, n = 6;
$^b$based on the OVA content in the polymer
ASM-1: 3.2% w/w Al(OH)$_3$/3.5% w/w trehalose/0% w/w diethyl phthalate (DEP)/PLGA microspheres
ASM-2: 3.2% w/w Al(OH)$_3$/3.5% w/w trehalose/2.5% w/w DEP/PLGA microspheres
ASM-3: 3.2% w/w Al(OH)$_3$/3.5% w/w trehalose/5% w/w % DEP/PLGA microspheres With 400 μg initial incubation mass of OVA from 1 mg/mL OVA, the active ASM PLGA microspheres self-microencapsulated about 200 μg (self-microencapsulation capacity=1% w/w (OVA/polymer matrix)) thereby exhibiting self-microencapsulation efficiency of about 50% (Table 4).

The similar loading of the three preparations (ASM-1, ASM-2, and ASM-3) also indicated that the protein loading was governed by the effective capacity of the Al(OH)$_3$ for sorbing OVA when the external OVA content exceeded the Al(OH)$_3$ sorbing capacity available in the polymer. Therefore, the encapsulation efficiency was further increased by decreasing external OVA content to roughly that encapsulated (~200 μg) previously, that is, by incubating microspheres with 200 μg OVA from 0.5 mg/mL OVA. As expected, ASM-1, ASM-2, and ASM-3 microspheres self-microencapsulated almost the entire OVA mass, thereby exhibiting extraordinary self-microencapsulation efficiency (96-98%) (Table 4). The potential of active SM PLGA microspheres to actively self-microencapsulate very sensitive vaccine antigen (TT) after sterilization of blank microspheres with gamma radiations was investigated and compared with the results obtained prior to irradiation (Table 5). There was no significant difference in active loading of TT before and after sterilization of active SM PLGA microspheres, indicating the effectiveness of this novel strategy to self-encapsulate vaccine antigens after terminal sterilization of microspheres. For example, with 400 μg initial incubation mass of TT from 0.8 mg/mL loading solution, all the active SM PLGA microsphere formulations self-encapsulated TT equivalent to about 1.6% w/w polymer loading and 87% encapsulation efficiency (3 measurements).

TABLE 5

Effect of gamma irradiation of active self-microencapsulating PLGA microspheres on active loading and encapsulation efficiency of tetanus toxoid (TT).

| | Initial TT mass[a] (µg) | Remaining TT mass[a] (µg)* | TT loaded (µg)* | TT Loading[b] (% w/w)* | Encapsulation efficiency[b] (%)* |
|---|---|---|---|---|---|
| Unencapsulated Al(OH)$_3$[c] | 400 | 0.0 | 400.0 ± 0.0 | — | — |
| Before irradiation | | | | | |
| ASM-1 | 400 | 53.7 ± 1.9 | 346.3 ± 1.9 | 1.62 ± 0.02 | 86.6 ± 0.5 |
| ASM-2 | 400 | 52.2 ± 1.4 | 347.8 ± 1.4 | 1.66 ± 0.03 | 86.9 ± 0.4 |
| After irradiation[d] | | | | | |
| ASM-1 | 400 | 52.8 ± 1.2 | 347.2 ± 1.2 | 1.64 ± 0.03 | 86.8 ± 0.3 |
| ASM-2 | 400 | 53.2 ± 0.6 | 346.8 ± 0.6 | 1.61 ± 0.03 | 86.7 ± 0.2 |

[a]volume = 0.5 mL;
*Mean ± SE, n = 3;
[b]based on the TT mass loss from solution;
[c]mass of Al(OH)$_3$ = 0.6 mg
ASM-1: 3.2% w/w Al(OH)$_3$/3.5% w/w trehalose/0% w/w diethyl phthalate (DEP)/PLGA microspheres
ASM-2: 3.2% w/w Al(OH)$_3$/3.5% w/w trehalose/5% w/w DEP/PLGA microspheres;
[d]irradiation dose and dose rate were 2.5 MRad at 0.37 MRad/h.

The effect of encapsulation of Al(OH)$_3$ and blending of hydrophobic plasticizer (diethyl phthalate (DEP)) on the self-healing phenomenon of PLGA 50:50 ($M_w$=51 kDa) microspheres is shown in FIG. 7.

It is noted that the Al(OH)$_3$ gel appeared to suppress self-healing as pores still appeared after incubation of the active SM PLGA microspheres at 43° C. (FIG. 7) as compared to full healed microspheres prepared without Al(OH)$_3$ gel (FIG. 7). Hence, we sought to increase PLGA mobility by incorporating a hydrophobic plasticizer in the polymer. For example, diethyl phthalate (DEP) was blended with the polymer while preparing blank Al(OH)$_3$-PLGA microspheres. As expected, with increasing amount of hydrophobic plasticizer in PLGA, pore-closing (self-healing) at 37° C. was clearly visible in FIG. 7, indicating that any suppression of self-healing by Al(OH)$_3$ could be overcome by the hydrophobic plasticizer.

It can be emphasized that SM PLGA microspheres with respectively 3.2, 3.5, and 5% w/w of Al(OH)$_3$, trehalose and DEP were found to be an optimal formulation for active self-healing microencapsulation of protein at physiological temperature (37° C.) with high encapsulation efficiency. Moreover, the successful employment of DEP to reduce the required temperature for self-healing opens-up the door to self-microencapsulate temperature-sensitive molecules in higher $M_w$ PLGA at or below physiological temperature.

Evaluation of quality of active protein self-microencapsulation in Al(OH)$_3$-PLGA microspheres: Evaluation of quality of active protein self-encapsulation in Al(OH)$_3$-PLGA ($M_w$=51 kDa) (ASM PLGA) microspheres was tested first in 190 mM sodium citrate solution, a buffer commonly used to elute protein antigens completely from Al(OH)$_3$ adjuvant within 3 days. The release of OVA from active self-encapsulated Al(OH)$_3$-PLGA microspheres was significantly different (p<0.05) compared to unencapsulated Al(OH)$_3$ (FIG. 8). For example, ASM-3 PLGA microspheres (3.2% w/w Al(OH)$_3$/3.5% w/w trehalose/5% w/w DEP/PLGA microspheres) largely retained OVA (i.e., 60-73%) after 1-day of exposure to the citrate buffer, whereas unencapsulated Al(OH)$_3$ released all the protein (97±0.8% release). In addition, ASM-3 PLGA microspheres released OVA slowly in a controlled manner over a period of 10 days (48±4.4% release (three measurements) after 10 days), indicating an effective active self-encapsulation of protein in Al(OH)$_3$-PLGA microspheres. After 10 days of release duration, the remaining OVA (soluble and insoluble) in ASM-3 PLGA microspheres was recovered as described in the OVA recovery method. After 10 days of release, 47±6.4% soluble monomer and 5.8 ±0.8% insoluble aggregate (covalent and non-covalent) was recovered from ASM-3 PLGA microspheres with a total recovery of 100.8±0.8% (three measurements).

Long-term controlled release of proteins from ASM PLGA (Al(OH)$_3$-PLGA) microspheres: The potential of PLGA active self-encapsulation to provide long-term release of stable proteins was evaluated by assessing OVA monomer and antigenic TT release from unencapsulated Al(OH)$_3$ and active self-encapsulated without (ASM-1) and with (ASM-3) 5% w/w DEP-Al(OH)$_3$-PLGA microspheres (Tables 3-5) in PBS (pH 7.4) (FIG. 3C) or PBS+0.02% Tween™ 80+0.2% BSA (FIG. 3D) at 37° C. The release of OVA monomer or antigenic TT from ASM-3 PLGA microspheres (3.2% w/w Al(OH)$_3$/3.5% w/w trehalose/5% w/w DEP/ PLGA microspheres) was also significantly different (p<0.05) than unencapsulated Al(OH)$_3$ (FIG. 3C and D). For example, OVA-Al(OH)$_3$ control gel exhibited 76, 90, and 99% OVA monomer release and TT-Al(OH)$_3$ control gel exhibited 87, 95, and 98% antigenic TT release respectively after 1, 3, and 7 days. In contrast, ASM-3 PLGA microspheres exhibited very less initial burst (17% OVA monomer or 32% antigenic TT release after 1 day) and provided slow and continuous release of OVA monomer or antigenic TT over a period of 28 days (49 and 68% OVA monomer or 83 and 99% antigenic TT release respectively after 14 and 28 days). After 28 days of release, 19±3% soluble OVA monomer and 10±2% insoluble OVA aggregate (covalent and non-covalent) was recovered from ASM-3 PLGA microspheres with a total recovery of 98±3% (three measurements).

As the microencapsulation of vaccine antigens in Al(OH)$_3$-PLGA microspheres can be easily performed by simple of mixing of vaccine antigens/Al(OH)$_3$-PLGA microspheres and heating the mixture to physiological temperature (no harsh manufacturing conditions), this new approach opens-up a new mode for sustained vaccine delivery similar to a injectable peptide formulation (e.g., Lupron depot), thereby improving the stability and efficacy of vaccine antigens. Note that injectable PLGA microspheres represent an approach to control the release of vaccine antigens to reduce the number of doses in the immunization schedule and optimize the desired immune response via selective targeting of antigen to antigen presenting cells.

Accordingly, the present technology provides delivery systems having high encapsulation efficiencies for one or more various agents. The delivery system can include an ionic affinity trap, such as a metal salt, in combination with a solid polymer matrix to enable a large portion or substantially the entire amount of an agent outside the polymer to enter pores in the polymer, for example, where the agent is subsequently encapsulated following self-healing of the polymer.

The delivery system includes a solid polymer matrix. The solid polymer matrix can include a polymer, such as a self-healing polymer, and can include one or more pores, an ionic affinity trap, an agent, and anything else associated with the delivery system. For example, the solid polymer matrix can include a self-healing polymer that includes one or more pores including an ionic affinity trap that can be used to sorb an agent, where the pores are then partially or completely closed to encapsulate the agent and prevent it from leaving the pore(s). The polymer can include a porous self-healing polymer that is able to alter its shape following a treatment. For example, open pores within the self-healing polymer can partially or completely close following a temperature change to sequester contents of the pores. Encapsulation efficiencies greater than 99% can be achieved. A further advantage is that the solution concentration of the agent to be encapsulated can be less than the concentration used in passive methods; e.g., about 1 mg/mL of agent in the present methods versus roughly 100 mg/mL or greater amounts of agent in passive methods. This opens the door to encapsulate an agent having a low aqueous solubility and/or an agent that is only available in limited quantities. Likewise, the amount of residual agent left in the solution following encapsulation can be significantly decreased, thereby making the present methods more proficient and economical. In some embodiments, the delivery system comprises a self-healing polymer, where a portion of the self-healing polymer comprises ionized end groups and an agent sorbed to the ionized end groups.

Various embodiments of the present technology can include the following aspects. The self-healing polymer can be biodegradable and can degrade or erode over time. The ionic affinity trap may also act as an adjuvant in some cases. The delivery system can further include the use of a plasticizer to plasticize the polymeric material and manipulate the temperature at which self-healing begins to occur. Control of these properties can be important for encapsulation of certain agents that may be damaged at elevated temperatures (e.g., 43° C. or higher) commonly used with moderate molecular weight self-healing polymers.

In some embodiments, the delivery system can include a porous self-healing polymer, optionally a differentially soluble material such as a saccharide or disaccharide, and one or more ionic affinity traps and plasticizers. The differentially soluble material can be employed to obtain a porous self-healing polymer network and/or to stabilize the polymeric material. The ionic affinity trap and plasticizer can improve the encapsulation efficiency and the self-healing property of the polymer, respectively. A self-healing polymer having a porous network, such as PLGA microspheres, can be prepared using established methods, such as those described in U.S. Pat. Appl. Pub. 2008/0131478 to Schwendeman et al.; Sophocleous et al., J. of Controlled Release 137 (2009) 179-184; Kang et al., Molecular Pharmaceutics, vol. 4, no. 1, 104-118 (2007); Cui et al., Vaccine 25 (2007) 500-509; and Jiang et al., Advanced Drug Delivery Reviews 57 (2005) 391-410.

In accordance with the present methods, a solution comprising an agent is placed in contact with a self-healing polymer having pores or one that can form pores when in contact with the solution. At the same time or following a soaking period, the self-healing polymer experiences a condition that causes spontaneous polymer chain rearrangement, which in turn causes the accessible pores (pores having access to the polymer surface) to close. The agent becomes entrapped, encapsulated, or absorbed within the self-healing polymer when these pores close.

In some embodiments, the self-healing polymer can be: poly(dicyclopentadiene); poly(dimethyl siloxane); poly(diethoxy siloxane); furan-maleimide-based polymers; dicyclopentadiene-based polymers; anthracene-maleimide based polymers; 1,1,1-tris-(cinnamoyloxymethyl) ethane (TCE)-based polymers; poly(ethylene-co-butylene); methyl methacrylate (MMA) embedded polypropylene fibers; epoxy with a urea-formaldehyde microcapsule; ionomers including hydrocarbon polymers bearing pendant carboxylic acid groups that are either partially or completely neutralized with metal or quaternary ammonium ions (e.g., Surlyn 8920, Surlyn 8940, Nucrel 960, and Nucrel 925); epoxy resins-diglycidyl ether of bisphenol A, diglycidyl ether of bisphenol F; and combinations thereof. Also included are self-healing polymeric materials having reactive furfuryl functionality, including poly(furfuryl methacrylate) and poly(furfuryl methacrylate)-co-poly(methyl methacrylate), as described by Kavitha et al., Applied Materials & Interfaces, vol. 1, no. 7, 1427-1436 (2009). Also included are self-healing polymeric materials based on furan-functionalized, alternating thermosetting poly ketones and bis-maleimide, as described by Zhang et al., Macromolecules 2009, 42, 1906-1912. The polymeric material can also be a biodegradable material. And the polymeric material can be in several forms, including particles such as particles, including microspheres, and various shapes of tissue engineering scaffolds.

In some embodiments, the self-healing polymer can be copolymers of lactic acid and glycolic acid (PLGA) and related copolymers, including any polymer containing a polyester with lactic and/or glycolic acid repeat units. The polymers may be made using any method, and may be linear, star, branched, cross-linked, or any configuration so long as the polymer has lactic and/or glycolic repeat units, which may be liberated by hydrolysis. In accordance with the methods described herein, the pore-containing polymers may be preformed prior to the encapsulation step; i.e., the microparticles, micro spheres, tissue engineering scaffold, nanoparticles, drug-eluting stent, suture, or screw may be formed according to known methods prior to contact with the agent to be encapsulated.

PLGA is a polyester composed of one or more of three different hydroxy acid monomers, d-lactic, l-lactic, and/or glycolic acids. In general, the polymer, can be made to be highly crystalline (e.g., poly(l-lactic acid)), or completely amorphous (e.g., poly(d,l-lactic-co-glycolic acid)), can be processed into most any shape and size (e.g., down to <200 nm), and can encapsulate molecules of virtually any size. PLGA microspheres and other injectable implants have an established safety record and are used in several different marketed products from various companies worldwide. For example, these controlled-release products are capable of controlling the release of peptides and proteins slowly and continuously from about 1 to 6 months, or even longer.

In addition to the depot effect, smaller PLGA microparticles (e.g., less than 10 μm) have demonstrated adjuvant activity via their uptake by macrophages and dendritic cells (DCs), and their localization in lymph nodes, and to induce cytotoxic T lymphocyte (CTL) responses. For example, despite the biocompatibility of PLGA, the mild inflammatory response produced by PLGA microspheres is hypothesized as being involved in their adjuvant characteristics. Most significant are reports of long-lasting antibody responses, many neutralizing above protective levels, in numerous animal models following a single dose of PLGA microparticle encapsulated antigens including displays of immunological memory after 1 year of immunization and protection against challenge.

PLGA can be in the form of particles, such as microspheres, which can be prepared using a double emulsion-solvent evaporation microencapsulation method. For example, PLGA along with a saccharide or disaccharide, such as trehalose, and $CH_2Cl_2$ can be homogenized at 10,000 rpm using a Tempest IQ2 homogenizer (The VirTis Company, Gardiner, N.Y.) equipped with a 10 mm shaft in an ice/water bath for 1 min to prepare the first emulsion. Two milliliters of 5% (w/v) PVA solution can then be immediately added to the first emulsion and the mixture vortexed (Genie 2, Fisher Scientific Industries, Inc., Bohemia, N.Y.) for 15 sec. to produce the w/o/w double emulsion. The resulting emulsion can be poured into 100 mL of 0.5% (w/v) PVA solution under rapid stirring and hardened at room temperature for about 3 hours. Hardened microspheres can be collected by centrifugation, washed three times with purified water, and freeze-dried. For freeze-drying, samples can be flash-frozen in liquid nitrogen and placed on a Freezone 6 freeze-drying system (Labcono, Kansas City, Mo.) at $133 \times 10^{-3}$ mbar or less vacuum at a condenser temperature of −46° C. for 48 hours. Three percent $MgCO_3$ powder (w/w of polymer) can suspended in the polymer solution before encapsulation when ionic affinity trap-containing PLGA microspheres are desired.

Morphology and size distribution of the microspheres can by ascertained by scanning electron microscopy. For example, microspheres can be first coated with gold for 200 sec. by a vacuum coater (Desk II, Denton Vacuum, Inc., Hill, N.J.). Microsphere morphology can then be observed using a scanning electron microscope (S3200N Variable Pressure SEM, Hitachi) with a voltage of 15 keV. For size distribution analysis, the size of more than 200 particles can be measured from SEM micrographs and the weight-averaged mean radius of the microspheres can be calculated. To observe the microsphere cross section, polymer specimens can be pre-cut by a razor blade on a glass slide before coating with gold.

In some embodiments, the delivery system can be prepared as follows. PLGA microparticles loaded with an ionic affinity trap (e.g., Alhydrogel) can be prepared by a water/oil/water (w/o/w) emulsion method. Briefly, alhydrogel can be concentrated to the desired concentration by removing water. Trehalose solutions (double the required concentration) can be prepared by dissolving the required amount in 50 mM succinate buffer. Alhydrogel and trehalose can then be mixed at 1:1 (v/v) ratio. Polymer solution (1 mL) can be prepared by dissolving the required amount of PLGA (250 or 350 mg/mL) in methylene chloride. About 200 or 300 μL of initial water phase can be added to PLGA solution followed by homogenization at 17,000 rpm for 60 seconds. Then, 2 mL of 5% PVA (9-10k, 80% hydrolyzed) can be immediately added to the mixture and vortexed for 50 seconds. The resulting emulsion can then be poured into 100 mL of 0.5% PVA (9-10k, 80% hydrolyzed) under continuous stirring. The resulting microspheres can be stirred for about 3 hours at room temperature, collected and washed thoroughly by passing through sieves of different mesh size. Microspheres can then be flash-frozen with liquid nitrogen and immediately freeze-dried.

Before encapsulation of an agent, the self-healing material comprising the self-healing polymer can be acceptably terminally sterilized (e.g., by gamma irradiation) with little or no loss in polymer molecular weight. A sterile solution of agent and sterile microspheres of polymeric material can then be combined to effect encapsulation. In some cases, a sterile agent solution can be added to sterile and dry microspheres.

During micro sphere formation, the polymer can be subjected to numerous stresses (e.g., excess heat, mixing, etc.) that normally cannot be used after loading the agent because certain agents (e.g., peptide/protein/DNA) may degrade under such conditions. In addition, the element of control over the ultimate polymeric material morphology and the kind of microsphere prepared can be vastly increased if encapsulation is performed after micro sphere (scaffold) preparation.

In some embodiments, the self-healing polymer can be in various configurations, and is not limited to particles or microspheres, for example. The self-healing polymer can be formed in various shapes and articles of various sizes. For example, the self-healing polymer can be used as a polymer coating on drug-eluting stents, prepared as nanopartices, and formed into tissue engineering scaffolds, including shapes that replace portions of tissue or shapes that conform to various tissues. For example, the materials and methods provided herein are also applicable to self-healing materials used as tissue engineering scaffolds, as well as any type of biomaterial or any other polymer encapsulation system (e.g., agricultural) that requires the need to encapsulate molecules that do not strongly partition into the polymer phase, but instead are encapsulated within the pores of a self-healing polymer. This is particularly useful for aqueous-based materials such as biological materials present in their native state in aqueous solution.

To load the microspheres, the microspheres can be incubated in an aqueous solution comprising an agent, where the agent can be at a fairly low concentration (e.g., about 0.5 to 1 mg/mL). The aqueous mixture of polymeric material and agent can then be incubated between about 10° C. to about 43° C. over a period of time, for example, ranging from hours to days. During this incubation, the porous network of the polymeric material heals thereby encapsulating the agent with a high encapsulation efficiency (e.g., >99%). Incubation temperature for loading the agent into the delivery system varies as the composition of the polymeric material varies; e.g., with or without an plasticizer. The incubating temperature can be tuned from about 10° C. to about 43° C. to achieve a very high encapsulation efficiency of the agent and to improve the self-healing property of the polymer. With the use of plasticizer, for example, self-healing of a moderate molecular weight polymer can occur readily at about 37° C. instead of about 43° C.

Thus, the self-healing polymer can be combined with a solution comprising an agent at a relatively low concentration, where nearly the entire amount of agent is taken up into the polymer pores, and the agent is then encapsulated within the polymer following self-healing of the polymer, where each step includes applying an appropriate temperature adjustment.

In some embodiments, the encapsulation efficiency (weight of agent encapsulated/weight agent in solution exposed to polymer) is greater than 50%. In some embodiments, the encapsulation efficiency is greater than 60%. In some embodiments, the encapsulation efficiency is greater than 70%. In some embodiments, the encapsulation efficiency is greater than 80%. In some embodiments, the encapsulation efficiency is greater than 90%. In some embodiments, the encapsulation efficiency is greater than 95%. And in some embodiments, the encapsulation efficiency is greater than 99%.

A differentially soluble material, such as a saccharide or similar material, can be used in forming the pores in the self-healing polymeric material. For example, after forming microparticles from a mixture of saccharide and polymer, the saccharide portion can be dissolved without dissolving the polymer to leave empty pores in the polymer. Useful saccharides include disaccharides such as trehalose, sucrose, and lactose. Other saccharides that can be used include polysaccharides, such as dextran, and glycosaminoglycans, such as heparin. The saccharide can be used to stabilize an ionomer gel used as the ionic affinity trap, for example, as described by A L Clausi, S A Merkley, JF Carpenter, T W Randolph, J Pharm Sci 97, 2049 (2008). Other pore-forming saccharides that can be used include mannose and mannitol.

In some embodiments, the differentially soluble material can include a water-soluble osmotic material in order to create the pores in a porous self-healing polymer. For example, Mg and Al salts can be used to create a percolating pore network; i.e., pores that interconnect with the surface of the polymer. Other basic salts are described by Zhu et al. in Pharmaceutical Research, Vol. 17, No. 3, 2000. For example, useful components for making pores and/or stabilizing proteins include those described in S. E. Bondos, A. Bicknell, Analytical Biochemistry 316 (2003) 223-231. Examples of such materials that may promote protein solubility include: kosmotropes including $MgSO_4$ at 0-0.4 M, $NH_4SO_4$ at 0-0.3 M, $Na_2SO_4$ at 0-0.2 M, $Cs_2SO_4$ at 0-0.2 M; weak kosmotropes including NaCl 0-1 M, KCl 0-1 M; Chaotropes including $CaCl_2$ 0-0.2 M, MgCl2 0-0.2 M, LiCl 0-0.8 M, RbCl 0-0.8 M, NaSCN 0-0.2 M, NaI 0-0.4 M, NaClO4 0-0.4 M, NaBr 0-0.4 M, Urea 0-1.5 M; Amino acids including glycine 0.5-2%, L-arginine 0-5 M; sugars and polyhydric alcohols including Sucrose 0-1 M, Glucose 0-2 M, Lactose 0.1-0.5 M, Ethylene glycol 0-60% v/v, Xylitol 0-30% w/v, Mannitol 0-15% w/v, Inositol 0-10% w/v, Sorbitol 0-40% w/v, Glycerol 5-40% v/v; Detergents including Tween 80 0-0.2% w/v, Tween 20 0-1201M, and Nonidet P-40 0-1%; and combinations thereof.

Ionic affinity traps used to sorb an agent in the present delivery systems include bases such as metal salts and metal hydroxides. The ionic affinity trap may also be in the form of a gel and can include various ionomers. For example, aluminum hydroxide and calcium phosphate gels are known as ionomers. Of the various metal salts and hydroxides, aluminum hydroxide and aluminum phosphate are two such ionic affinity traps that are particularly useful. Some ionic affinity traps may further act as an adjuvant to stimulate the immune system and increase the response to a vaccine. For example, where the agent is a macromolecule such as a protein antigen, the ionic affinity trap may also perform as an adjuvant when the delivery system is used for vaccination.

In some embodiments, the ionic affinity trap can include aluminum hydroxide and/or aluminum phosphate. Commercial forms of aluminum hydroxide (Alhydrogel™, 2%) and aluminum phosphate (Adju-Phos™) are available from Accurate Chemical and Scientific Corporation (Westbury, N.Y.). These aluminum materials can also act as adjuvants when the present delivery system is used with or as a vaccine. Aluminum hydroxide and aluminum phosphate can be prepared by exposing aqueous solutions of aluminum ions to alkaline conditions under very controlled circumstances, which in the case of aluminum phosphate takes place in the presence of phosphate ions. Various soluble aluminum salts can be used for the production of the ionic affinity trap, but the experimental conditions—temperature, concentration and even rate of addition of reagents—can strongly influence the results. Other metal salts that can be used as an ionic affinity trap include those disclosed in Zhu et al. in Pharmaceutical Research, Vol. 17, No. 3, 2000.

Colloidal or sub-colloidal suspensions of aluminum hydroxide can be characterized by particle size distribution, electrical charge, and the hydrated colloid nature of the precipitate formed. Alterations of the preparation recipe can give rise to various forms of aluminum hydroxide which differ with respect to their physico-chemical characteristics, stability and protein adsorption.

Several models for the structure of aluminum hydroxide exist. One model takes form in a ring-structure of six members, each member consisting of an $Al^{3+}$ surrounded by six coordinated water molecules in an octahedral shape. The coordinated water molecules are oriented with the oxygen toward the aluminum ion. The high charge of the $Al^{3+}$ is believed to weaken the bond between oxygen and hydrogen thus facilitating the removal of protons, especially under alkaline conditions. Deprotonization, thus facilitated by the alkalinity, is believed to lead to the initial formation of dimers by dihydroxyl bridges between octohedras and later to the formation of the six-membered ring-structure and even larger structures. In this process, the ratio of aluminium to hydroxide approaches 1:3. On the basis of this model the chemical formula $Al(OH)_3$ is misleadingly simple. The model thus described is a generalized model that does not consider crystalline forms or inclusion of other ions. When inclusion of other ions, originating from the salts used in the preparation, is taken into consideration aluminium hydroxide precipitated from aluminium chloride can be described as $Al(OH)_{2.55}(Cl)_{0.45}$, existing as a polymer of ten fused six-membered rings and if precipitated from sulphate as $Al(OH)_{2.30}(SO4)_{0.35}$ and based on three fused such rings.

When X-ray crystallography and IR spectroscopy are applied to aluminium gel preparations, a boehmite-like (aluminium oxyhydroxide) pattern is seen in preparations known as aluminium hydroxide, whereas commercialized aluminium phosphate gel adjuvant is identified as amorphous aluminium hydroxyphosphate. It is possible to calculate an average primary crystallite size of 4.5 nm×2.2 nm×10 nm for boehmite preparations.

The ionic affinity trap can bind agents such as proteins, including protein antigens, where the ionic affinity trap can be an aluminum salt adjuvant. Without the use of such adjuvants, proteins may be only weakly immunogenic. Aluminum salts are currently the only adjuvants generally approved for use in vaccines for humans. Despite their approved use, the mechanism of action is still poorly understood. Among a variety of nonmutually exclusive proposed mechanisms, roles as depots for antigen induction of inflammatory responses and delivery of antigen into antigen presenting cells are proposed.

The two most common aluminum salts employed as adjuvants are the phosphate and hydroxide forms. The salts themselves have been well characterized with aluminum hydroxide (Alhydrogel™) can usually be found in a crystalline state, whereas aluminum phosphate can exist in an amorphous form. The points of zero charge (analogous to the isoelectric point of a macromolecule) are 4.0-5.5 and about 11 for the phosphate and hydroxide salts, respectively. In general, proteins seem to better adsorb to the oppositely charged salts through simple electrostatic effects, although apolar and ion displacement interactions may play a role as well.

What happens to the structure and stability of proteins when they are adsorbed onto the surface of these two commonly employed aluminum salts is not well characterized. When proteins are adsorbed to solid surfaces, highly polar (including charged) interfaces tend to minimally perturb protein structure and stability, although exceptions are known. In contrast, more apolar surfaces often significantly alter the structure and stability of many proteins. The effect of the aluminum salt on protein structure and stability is important from several perspectives. For example, to the extent that epitopes are conformational in nature, their retention (or alteration) may be critical for vaccine immunogenicity. The stability of protein antigens is equally important when they are stored for long periods prior to their use. The latter strongly impacts the utility of vaccines for use in the developing world, where shipping under cold conditions can be problematic, and in the use of vaccines against potential bioterrorism agents, where storage for long periods in centralized locations may be critical for their effectiveness.

In some embodiments, the ionic affinity trap can be calcium phosphate. Calcium phosphate can function as an adjuvant and can be used to potentiate the immune response of vaccines and to prepare adsorbed allergen extracts. It can be well tolerated and readily resorbed by the body and it is believed to potentiate the immune response by the depot mechanism whereby the antigen is adsorbed during the preparation of the vaccine and slowly released following administration. Calcium phosphate is also believed to act by presenting the adsorbed antigen to antigen presenting cells as a particulate antigen.

Calcium phosphate has a molecular composition close to $Ca_3(PO_4)_2$, where the calcium/phosphorus molar ratio (Ca/P) can vary from 1.35 to 1.83 depending on the rate of mixing during the precipitation reaction. The properties of the precipitate are strongly dependent on the precipitation conditions. For example, calcium phosphate precipitated by rapid mixing can adsorb about 100% of diphtheria toxoid while calcium phosphate precipitated by slow mixing can adsorb about 58% of the same dose of diphtheria toxoid.

Preparations of calcium phosphate are available from Reheis Inc. (Berkeley Heights, N.J.) and Brenntag Biosector (Frederikssund, Denmark).

Although its name suggests that it is $Ca_3(PO_4)_2$, X-ray diffraction, FTIR spectroscopy, thermal analysis, and the Ca/P molar ratio identify commercial calcium phosphate as non-stoichiometric hydroxyapatite, $Ca_{10-x}(HPO4)_x(PO4)_{6-x}(OH)_{2-x}$, where x varies from 0 to 2. The surface charge is also pH-dependent (point of zero charge=5.5). Consequently, commercial calcium phosphate exhibits a negative surface charge at physiological pH and electrostatically adsorbs positively charged materials, such as positively charged antigens. The presence of hydroxyls can further allow calcium phosphate to adsorb phosphorylated antigens by ligand exchange with surface hydroxyls.

Another useful ionic affinity trap is aluminum phosphate. And in some embodiments, the ionic affinity trap can be alum, which includes aluminum and potassium.

Other examples of ionic affinity traps include extracellular matrix-like materials, including dextran sulfate, chitosan, and hyaluronic acid.

In some embodiments, there are a number of different ways to actively load the polymer. (1) Layer-by-layer assembly based on charge. For example, start with a negatively charged agent, such as heparin, inside the polymer pores and then bind heparin-binding growth factors; e.g., fibroblast growth factors and vascular endothelial growth factors. Alternating incubations of growth factor and heparin create a network of growth factor stabilized in between heparin layers; i.e., heparin-growth factor-heparin-growth factor and so on. (2) Creating a gradient of a substance from inside the polymer to outside that causes the protein to precipitate in the polymer; e.g., with ammonium sulfate inside the polymer. (3) Placing a nucleating agent for crystallization inside the polymer at a concentration above saturation; e.g., using features as described in U.S. Pat. No. 5,869,604. This includes using exogenous nucleating agents such as minerals, transition metal ions such as copper and lead, highly absorbent structures such as zeolites, preformed crystal seeds of amino acids, and preformed crystal seeds of polypeptides other than the agent being loaded into the pores. (4) Creating a Donnan equilibrium (e.g., charged species that can not escape the pores), forming a pH gradient, precipitating the protein at its isoelectric pH. (5) Addition of a counterion to the pores of the polymer that causes the protein to come out of solution as a stabilized insoluble salt; e.g., $Zn^{2+}$ insulin or $Zn^{2+}$ growth hormone using Zn acetate in the polymer. (6) Placing a porous polymer with evacuated pores in contact with a solution comprising the agent and releasing pressure so that the solution fills the pores.

A plasticizer can be used to plasticize the polymeric material and manipulate the temperature at which self-healing begins to occur. Useful plasticizers include diethyl phthalate, tributyl acetylcitrate, and similar compounds. Other useful plasticizers include those that (1) cause a pore network to form (e.g., by osmotic pressure), (2) stabilize the encapsulated molecule, and (3) cause the encapsulated molecule to preferentially distribute inside the polymer pores (e.g., either in solution, in solid state, or sorbed to a structure of some kind) relative to the outside solution.

The agent to be encapsulated may be any material, compound, or biomolecule of interest that can associate with the ionic affinity trap. The methods provided herein are particularly useful for agents that would be subject to degradation when exposed to conditions used in preparing pore-containing polymers. Examples of agents include biomolecules such as proteins, peptides, proteoglycans, lipoproteins, and nucleic acids, such as RNA and DNA. Some non-limiting examples of proteins that may be used with the present methods include bovine serum albumen, hen egg-white lysosome, ribonuclease A, growth hormone, tetanus toxoid, erythropoietin, insulin-like growth factor-I, vascular endothelial growth factor, bone morphogenetic protein, and basic fibroblast growth factor.

In some embodiments, the agent can be a small molecule or a large colloidal particle (e.g., virus), or any bioactive substance, such as a biomacromolecule. The only caveat is that the agent to be encapsulated should have an affinity for the ionic affinity trap. In this way, the agent can be present at a low concentration (e.g., 1 mg/mL or lower) so that the ionic affinity trap acts to bind and effectively load the porous polymeric material with the agent. Loading of the porous polymeric material is therefore not dependent on passive diffusion, which typically requires a high concentration of agent to be loaded in order to obtain the desired loading level.

The present technology may also be used for small molecules, e.g., drugs used in drug-eluting stents or in nanoparticle delivery. Hydrophilic molecules can be problematic to encapsulate in drug-eluting stents by conventional methods. The present technology may also be used to encapsulate nanoparticulate materials (e.g., viruses) without drying the polymer. For example, some materials may be denatured or degraded in whole or part by a drying process and hence the present methods can avoid drying is such instances.

To further illustrate the present technology, another example of PLGA microspheres loaded with ovalbumin can be prepared as follows to demonstrate an embodiment of a delivery system constructed in accordance with the present technology. The effects of formulation and incubation parameters on agent loading were ascertained indicated in Tables 6-13. Ovalbumin is used as a model to demonstrate loading of a protein antigen, for example. The following parameter effects were determined.

TABLE 6

Effect of alhydrogel loading (theoretical).

| Incubation Temperature and Time | | Ovalbumin Adsorbed (µg)* Alhydrogel Loading (Theoretical) | | | |
|---|---|---|---|---|---|
| T | t | (wt %) | | | |
| (° C.) | (h) | Blank | 0.7 | 1.3 | 3.2 |
| 25 | 3 | −0.7 ± 3.8 | 42.4 ± 2.4 | 70.9 ± 7.9 | 87.6 ± 2.8 |
|  | 6 | −4.0 ± 2.7 | 62.5 ± 4.9 | 73.0 ± 1.0 | 91.2 ± 1.7 |
|  | 24 | −7.1 ± 9.3 | 65.3 ± 9.9 | 77.8 ± 6.3 | 95.4 ± 1.9 |

*Mean ± S.E
Concentration of PLGA: 350 mg/mL;
Initial water phase: 200 µL
Trehalose loading: 7.8 wt %;
Microparticles size: 20-63 µm

TABLE 7

Effect of trehalose loading (theoretical).

| Incubation Temperature and Time | | Ovalbumin Adsorbed (µg)* Trehalose Loading (Theoretical) | | | |
|---|---|---|---|---|---|
| T | t | (wt %) | | | |
| (° C.) | (h) | 0 | 1.9 | 3.8 | 10.4 |
| 25 | 3 | 73.0 ± 7.1 | 75.1 ± 1.4 | 85.0 ± 2.8 | 84.2 ± 3.1 |
|  | 6 | 73.4 ± 5.3 | 82.7 ± 8.2 | 99.2 ± 3.3 | 85.5 ± 3.3 |
|  | 24 | 80.0 ± 2.8 | 104.2 ± 1.8 | 111.0 ± 5.5 | 88.0 ± 7.9 |

*Mean ± S.E
Concentration of PLGA: 250 mg/mL;
Initial water phase: 200 µL
Alhydrogel loading: 2.9 to 3.2 wt %;
Microparticles size: 20-63 µm

TABLE 8

Effect of volume of initial water phase.

| Incubation Temperature and Time | | Ovalbumin Adsorbed (µg)* Volume of Initial Water Phase | |
|---|---|---|---|
| T | t | (µL) | |
| (° C.) | (h) | 200 | 300 |
| 25 | 3 | 70.9 ± 7.9 | 50.7 ± 0.4 |
|  | 6 | 73.0 ± 1.0 | 68.1 ± 4.7 |
|  | 24 | 77.8 ± 6.3 | 73.2 ± 4.6 |

*Mean ± S.E
Concentration of PLGA: 350 mg/mL;
Alhydrogel loading: 1.35 and 1.93 wt %;
Trehalose loading: 7.8 wt %;
Microparticles size: 20-63 µm

TABLE 9

Effect of size of microparticles.

| Incubation Temperature and Time | | Ovalbumin Adsorbed (µg)* Size of Microparticles | |
|---|---|---|---|
| T | t | (µm) | |
| (° C.) | (h) | 20-63 | 63-90 |
| 25 | 3 | 75.4 ± 12.9 | 29.1 ± 9.0 |
|  | 6 | 79.5 ± 10.7 | 47.0 ± 9.7 |
|  | 24 | 92.3 ± 5.5 | 59.2 ± 4.3 |

*Mean ± S.E
Concentration of PLGA: 350 mg/mL;
Alhydrogel loading: 1.35 wt %
Trehalose loading: 14.4 wt %;
Initial water phase: 200 µL

TABLE 10

Effect of concentration of PLGA.

| Incubation Temperature and Time | | Ovalbumin Adsorbed (µg)* Concentration of PLGA | |
|---|---|---|---|
| T | t | (mg/mL) | |
| (° C.) | (h) | 250 | 350 |
| 25 | 3 | 84.2 ± 3.1 | 78.0 ± 5.8 |
|  | 6 | 85.5 ± 3.3 | 84.1 ± 2.3 |
|  | 24 | 88.0 ± 7.9 | 87.8 ± 4.1 |

*Mean ± S.E
Alhydrogel loading: 2.9 wt %;
Trehalose loading: 14.4 wt %
Initial water phase: 200 µL;
Microparticles size: 20-63 µm

TABLE 11

Effect of incubation temperature.

| Incubation Temperature and Time | | Ovalbumin Adsorbed (μg)* Incubation Temperature | |
|---|---|---|---|
| T (° C.) | t (h) | (° C.) | |
| | | 10 | 25 |
| 25 | 3 | 78.9 ± 2.6 | 85.0 ± 2.8 |
| | 6 | 83.3 ± 3.4 | 99.2 ± 3.3 |
| | 24 | 89.8 ± 2.5 | 111.0 ± 5.5 |

*Mean ± S.E
Concentration of PLGA: 250 mg/mL;
Alhydrogel loading: 3.2 wt %;
Trehalose loading: 3.8 wt %;
Initial water phase: 200 μL;
Microparticles size: 20-63 μm

TABLE 12

Effect of adjuvant type.

| Incubation Temperature and Time | | Ovalbumin Adsorbed (μg)* Adjuvant Type | |
|---|---|---|---|
| T (° C.) | t (h) | Aluminum Hydroxide | Calcium Phosphate |
| 25 | 3 | 78.9 ± 2.6 | 55.7 ± 5.4 |
| | 6 | 83.3 ± 3.4 | 58.7 ± 5.0 |
| | 24 | 89.8 ± 2.5 | 82.0 ± 9.7 |

*Mean ± S.E
Concentration of PLGA: 250 mg/mL;
Alhydrogel loading: 3.2 wt %;
Calcium Phosphate loading: 3.4 wt %;
Trehalose loading: 3.8 wt %;
Initial water phase: 200 μL;
Microparticles size: 20-63 μm

TABLE 13

Recovery of ovalbumin after release study in 194 mM Sodium citrate.

| Formulation | Ovalbumin Released after 10 days (%) | Ovalbumin Recovered from polymer after 10 days (%) | Insoluble aggregate (covalent and noncovalent) (%) | Total Recovery (%) |
|---|---|---|---|---|
| 3.2 wt % Alhydrogel/PLGA | 78.3 ± 4.6 | 21.0 ± 4.2 | 1.3 ± 0.2 | 100.6 ± 0.2 |
| 3.1 wt % Alhydrogel/5 wt % DEP/PLA | 47.9 ± 4.4 | 47.1 ± 6.4 | 5.8 ± 0.8 | 100.8 ± 0.8 |

Self-healing of microparticles loaded with ovalbumin is further illustrated in FIGS. 9-11. FIG. 9 depicts 3.2 wt % Alhydrogel/3.8 wt % Trehalose/PLGA microparticles before (A) and after (B) self-healing by incubating at about 25° C. for about 24 hours and about 43° C. for about 48 hours. FIG. 10 depicts 3.2 wt % Alhydrogel/3.8 wt % Trehalose/2.5 wt % DEP/PLGA microparticles before (A) and after (B) self-healing by incubating at about 10° C. for about 48 hours, at about 25° C. for about 24 hours, and at about 37° C. for about 30 hours. FIG. 11 depicts 3.2 wt % Alhydrogel/3.8 wt % Trehalose/5 wt % DEP/PLGA microparticles before (A) and after (B) self-healing.

In another example of the present technology, a delivery system is used to microencapsulate Leuprolide, a potent agonistic analogue of luteinizing hormone-releasing hormone, inhibits the secretion of pituitary gonadotropin when administered chronically in therapeutic doses. Microsphere depot formulations of leuprolide can be developed for long-term testosterone suppression.

In some embodiments, the present technology can employ "sorption loading." Basically, this involves taking ground PLGA of relatively low MW (from the manufacturer), which has ionized end group (in this case carboxylate, but could be made anything), and then incubating low peptide solution concentrations. The ionic interaction causes the peptide to "sorb" to the polymer. The full nature of this sorption is not fully understood, other than it requires the ionized end group and a high enough temperature for polymer chain mobility. It could be mostly at the surface, i.e., adsorption, or mostly in the bulk, i.e., absorption. The sorption group in FIG. 13 is generated with injections every two, three, or four weeks at the same dosage as the Lupron Depot. The polymer is of low MW and takes up more water than the polymers generated for most self-healing microencapsulation methods. In this example, we expect the peptide sorbs by penetration directly into the polymer phase and combines with carboxylic end groups (the ionic affinity trap), as the acid end-group PLGA takes up sufficient water for peptide permeation.

Evaluation of long-term testosterone suppression ability of leuprolide acetate (LA)-PLGA particles in male Sprague-Dawley rats was performed as follows.

The efficacy of LA-PLGA particles to provide long-term in vivo LA release was evaluated by assessing long-term testosterone suppression ability of LA-PLGA particles in male Sprague-Dawley rats. The treatment of experimental animals was in accordance with University committee on use and care of animals (University of Michigan UCUCA), and all NIH guidelines for the care and use of laboratory animals. Male Sprague-Dawley rats of 6 weeks old were housed in cages and given free access to standard laboratory food and water, and allowed one week to acclimate prior to study initiation. Animals were anesthetized with 2-4% isoflurane administered by a calibrated vaporizer (Midmark, Orchard Park, N.Y., USA). The leuprolide acetate (1×) and LA-PLGA particles (2× (day 0, 14, 28, and 42), 3× (day 0, 21, and 42), and 4× (day 0 and 28) in a liquid vehicle (1% w/v carboxymethylcellulose and 2% w/v mannitol), and commercial Lupron Depot (2X (day 0 and 28)) were subcutaneously injected at the back (lower neck portion) of rats (6 animals/study group). The dose of leuprolide acetate was 100 μg/kg/day. Animal body weight considered for dosing leuprolide acetate was 425 g which is projected body weight of male Sprague Dawley rat at midpoint (day 28) of the study (as per the weight (g)/age (weeks) curve given by Charles River Laboratories). Blood samples were collected via jugular vein stick before (day −7 and 0 for baseline testosterone level) and after (1, 7, 14, 21, 28, 35, 42, 49, and 56 days) injection of preparations. The collected blood samples were immediately transferred to B-D Microtainer™ blood collection and serum separation tubes previously incubated in ice, centrifuged at 8,000 rpm for 10 min, and then the serum was removed and stored in microcentrifuge tubes at −20° C. until further use. Serum testosterone levels were assayed by Radioimmunoassay using a TESTOSTERONE Double Antibody-1251 RIA Kit (MP Biomedicals LLC., Solon, Ohio, USA) at the University of Pennsylvania Diabetes Center (Philadelphia, Pa., USA). Lowest detection limit of testosterone was 0.1 ng/mL.

The following methods were employed. Aspects of leuprolide acetate (LA) sorption by PLGA particles include the following. Previously grinded and sieved (20-63 μm) PLGA was used for the absorption of LA to PLGA. Solution (3 mM) of LA in HEPES (0.1 M, pH 7.4) was added to PLGA particles (1 mL/10 mg particles) and incubated on a rotary shaker at 37° C. After 6 h of incubation, LA equivalent to 1 mM was added to boost the concentration gradient and hence LA absorption to PLGA. After 24 h incubation, LA/PLGA particles mixture was centrifuged at 8000 rpm for 10 min and supernatant was removed. The residual particles were washed three times with deionized water (1 mL water/10 mg particles) and then freeze-dried. LA absorbed PLGA particles were passed through sieves to obtain 20-63 μm and stored at -20° C. until further use.

Aspects of determining leuprolide acetate loading in leuprolide acetate-PLGA particles include the following. LA content in LA-PLGA particles was determined by two-phase extraction. Briefly, about 10 mg LA absorbed PLGA 50:50 (Resomer® RG 502H) particles (n=3) were weighed into 5 mL glass vials. To these vials, 1 mL of methylene chloride and 2 mL of 50 mM sodium acetate (pH 4.0) were added, followed by vortexing for 1 min. One and half milliliter of buffer layer was removed, replaced with 1.5 mL of same buffer (5 extractions) or 50 mM sodium acetate+1 M NaCl (6 extractions) and similarly extracted for 11 times. The content of LA in each extracted fraction was then analyzed and quantified by HPLC. Eleven extractions found to be sufficient to remove LA completely from LA-PLGA complexes as the peak of LA disappeared in $12^{th}$ extraction.

Evaluation of in vitro release of leuprolide acetate from LA-PLGA particles was as follows. In vitro release of LA was performed under perfect sink condition. Briefly, about 10 mg LA-PLGA particles were weighed (n=3) into Eppendorf tubes and 1 mL of PBST+0.02% sodium azide was added. Eppendorf tubes were then incubated at 37 ° C. on a rotary shaker at 240 rpm. At specified time points (1-10 days and every two days thereafter), tubes were centrifuged at 8,000 rpm for 5 min and 1 mL supernatant was removed and then replaced with pre-warmed (37° C.) release medium. Analysis of LA in release samples was performed by HPLC.

The following results were obtained.

TABLE 14

Evaluation of leuprolide acetate (LA) content in LA-PLGA particles.

| | LA loading (wt %) | | | |
|---|---|---|---|---|
| Extraction method | Amino acid analysis method | LA loading efficiency (%) | LA absorbed (μmol/g PLGA) | Fraction of acids occupied[a] |
| 17.2 ± 2.2 | 17.0 ± 2.7 | 33.2 ± 0.1 | 140.8 ± 10.9 | 0.68 ± 0.05 |

[a]Fraction of acids occupied = LA absorbed/total acids of polymer (μmol/g PLGA).

In vitro release of leuprolide acetate from LA-PLGA particles is shown in FIG. 12.

In vivo testosterone suppression in male Sprague-Dawley rats by leuprolide acetate-PLGA particles is shown in FIG. 13.

Benefits of the current technology include: a) the ability to prepare agent encapsulated products in a straightforward manner, b) reduction in the cost of manufacturing as loss of expensive agents during encapsulation is reduced and a smaller quantity of agent (about 0.5 to 1 mg/mL) can be used to achieve very high encapsulation efficiency (99% or more), c) can be used with multiple agents, d) can be used at point-of-care, and e) allows terminal sterilization of the delivery system prior to agent loading (i.e., no aseptic manufacturing with organic solvents is required).

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

The following non-limiting discussion of terminology is provided with respect to the present technology.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "desire" or "desirable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9,1-8,1-3,1-2,2-10, 2-8, 2-3,3-10, and 3-9.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters.

When an element or layer is referred to as being "on," "engaged to," "connected to" or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

What is claimed is:

1. A method of making a delivery system comprising:
providing a biodegradable polymer matrix having an interconnected porous structure and an ionic affinity trap disposed within the pores of the porous structure, and no agent disposed within the porous structure;
absorbing an agent into the polymer matrix from a surrounding aqueous solution;
reversibly binding the agent to the ionic affinity trap; and
increasing the temperature of the biodegradable polymer matrix to at least its hydrated Tg and thereby partially or fully encapsulating the agent, wherein the agent is encapsulated at >50% encapsulation efficiency; wherein said agent comprises a biomolecule, drug, or antigen, and wherein said ionic affinity trap comprises aluminum hydroxide, aluminum phosphate, calcium phosphate, or alum,
wherein the providing a biodegradable polymer matrix having an interconnected porous structure and an ionic affinity trap disposed within the pores of the porous structure comprises preparing a water-in-oil-in-water double emulsion wherein the initial water phase comprises a porosigen and the ionic affinity trap and the oil phase comprises the biodegradable polymer.

2. The method of claim 1, wherein the biodegradable polymer matrix comprises a copolymer of lactic acid and glycolic acid.

3. The method of claim 2, wherein the ionic affinity trap comprises $Al(OH)_3$ gel.

4. The method of claim 1, wherein the biomolecule comprises a protein, peptide, proteoglycan, lipoprotein, or nucleic acid.

5. The method of claim 1, wherein the biodegradable polymer matrix further comprises a plasticizer.

6. The method of claim 1, wherein the aqueous solution comprises less than about 5 mg/mL of the agent.

7. The method of claim 1, wherein the agent is encapsulated at greater than 90% encapsulation efficiency.

8. The method of claim 2 wherein the biodegradable polymer matrix comprises poly(D,L-lactic-co-glycolic acid) 50:50.

9. The method of claim 5 wherein the plasticizer comprises diethyl phthalate.

10. The method according to claim 1, wherein the ionic affinity trap comprises $Ca_3(PO_4)_2$ or non-stoichiometric hydroxyapatite, $Ca_{10-x}(HPO_4)_x (PO_4)_{6-x}(OH)_{2-x}$, where x varies from 0 to 2.

11. The method according to claim 1, wherein the ionic affinity trap comprises aluminum phosphate.

12. The method according to claim 1, wherein the ionic affinity trap comprises alum.

13. The method according to claim 1, wherein the ionic affinity trap comprises an ionomeric gel.

* * * * *